US012751649B2

(12) United States Patent
Taub et al.

(10) Patent No.: US 12,751,649 B2
(45) Date of Patent: Oct. 6, 2026

(54) ANALYTE MONITORING AND MANAGEMENT DEVICE AND METHOD TO ANALYZE THE FREQUENCY OF USER INTERACTION WITH THE DEVICE

(71) Applicant: ABBOTT DIABETES CARE INC., Alameda, CA (US)

(72) Inventors: Marc Barry Taub, Mountain View, CA (US); Jolyon Robert Bugler, Combe (GB); Thomas A. Peyser, Menlo Park, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 1487 days.

(21) Appl. No.: 17/113,560

(22) Filed: Dec. 7, 2020

(65) Prior Publication Data

US 2021/0169384 A1 Jun. 10, 2021

Related U.S. Application Data

(63) Continuation of application No. 15/916,255, filed on Mar. 8, 2018, now Pat. No. 10,856,785, which is a continuation of application No. 14/629,447, filed on Feb. 23, 2015, now Pat. No. 9,913,600, which is a continuation of application No. 13/448,287, filed on Apr. 16, 2012, now abandoned, which is a
(Continued)

(51) Int. Cl.

| | |
|---|---|
| ***A61B 5/145*** | (2006.01) |
| ***A61B 5/00*** | (2006.01) |
| ***G06Q 50/22*** | (2024.01) |
| ***G16H 10/60*** | (2018.01) |
| ***G16H 40/67*** | (2018.01) |
| ***G16H 80/00*** | (2018.01) |

(52) U.S. Cl.
CPC ...... *A61B 5/14532* (2013.01); *A61B 5/14546* (2013.01); *A61B 5/7282* (2013.01); *A61B 5/746* (2013.01); *G06Q 50/22* (2013.01); *G16H 10/60* (2018.01); *G16H 40/67* (2018.01); *G16H 80/00* (2018.01); *A61B 5/7275* (2013.01)

(58) Field of Classification Search
CPC ............ A61B 5/14532; A61B 5/14546; A61B 5/7282; A61B 5/746; A61B 5/7275; G06Q 50/22; G16H 10/60; G16H 40/67; G16H 80/00
USPC .......................................... 600/309, 345–366
See application file for complete search history.

(56) References Cited

U.S. PATENT DOCUMENTS

| | | | |
|---|---|---|---|
| 3,581,062 | A | 5/1971 | Aston |
| 3,926,760 | A | 12/1975 | Allen et al. |
| 3,949,388 | A | 4/1976 | Fuller |

(Continued)

FOREIGN PATENT DOCUMENTS

| | | | |
|---|---|---|---|
| AU | 2020284312 | A1 | 12/2021 |
| DE | 4401400 | | 7/1995 |

(Continued)

OTHER PUBLICATIONS

U.S. Appl. No. 15/916,255, Nov. 18, 2020 Issue Notification.
(Continued)

*Primary Examiner* — Navin Natnithithadha
(74) *Attorney, Agent, or Firm* — Workman Nydegger

(57) ABSTRACT

Methods and Devices to monitor the level of at least one analyte are provided.

14 Claims, 5 Drawing Sheets

Related U.S. Application Data continuation of application No. 12/147,464, filed on Jun. 26, 2008, now Pat. No. 8,160,900.

(60) Provisional application No. 60/947,026, filed on Jun. 29, 2007.

(56) References Cited

U.S. PATENT DOCUMENTS 4,036,749 A 7/1977 Anderson
4,055,175 A 10/1977 Clemens et al.
4,082,086 A 4/1978 Page et al.
4,129,128 A 12/1978 McFarlane
4,245,634 A 1/1981 Albisser et al.
4,327,725 A 5/1982 Cortese et al.
4,344,438 A 8/1982 Schultz
4,349,728 A 9/1982 Phillips et al.
4,425,920 A 1/1984 Bourland et al.
4,441,968 A 4/1984 Emmer et al.
4,464,170 A 8/1984 Clemens et al.
4,478,976 A 10/1984 Goertz et al.
4,494,950 A 1/1985 Fischell
4,509,531 A 4/1985 Ward
4,527,240 A 7/1985 Kvitash
4,538,616 A 9/1985 Rogoff
4,545,382 A 10/1985 Higgins et al.
4,561,443 A 12/1985 Hogrefe et al.
4,619,793 A 10/1986 Lee
4,671,288 A 6/1987 Gough
4,703,756 A 11/1987 Gough et al.
4,711,245 A 12/1987 Higgins et al.
4,731,726 A 3/1988 Allen, III
4,749,985 A 6/1988 Corsberg
4,757,022 A 7/1988 Shults et al.
4,777,953 A 10/1988 Ash et al.
4,779,618 A 10/1988 Mund et al.
4,847,785 A 7/1989 Stephens
4,854,322 A 8/1989 Ash et al.
4,890,620 A 1/1990 Gough
4,925,268 A 5/1990 Iyer et al.
4,953,552 A 9/1990 DeMarzo
4,986,271 A 1/1991 Wilkins
4,995,402 A 2/1991 Smith et al.
5,000,180 A 3/1991 Kuypers et al.
5,002,054 A 3/1991 Ash et al.
5,019,974 A 5/1991 Beckers
5,047,044 A 9/1991 Smith et al.
5,050,612 A 9/1991 Matsumura
5,051,688 A 9/1991 Murase et al.
5,055,171 A 10/1991 Peck
5,082,550 A 1/1992 Rishpon et al.
5,106,365 A 4/1992 Hernandez
5,108,889 A 4/1992 Smith et al.
5,122,925 A 6/1992 Inpyn
5,135,004 A 8/1992 Adams et al.
5,165,407 A 11/1992 Wilson et al.
5,202,261 A 4/1993 Musho et al.
5,210,778 A 5/1993 Massart
5,228,449 A 7/1993 Christ et al.
5,231,988 A 8/1993 Wernicke et al.
5,246,867 A 9/1993 Lakowicz et al.
5,251,126 A 10/1993 Kahn et al.
5,262,035 A 11/1993 Gregg et al.
5,262,305 A 11/1993 Heller et al.
5,264,104 A 11/1993 Gregg et al.
5,264,105 A 11/1993 Gregg et al.
5,279,294 A 1/1994 Anderson et al.
5,285,792 A 2/1994 Sjoquist et al.
5,293,877 A 3/1994 O'Hara et al.
5,299,571 A 4/1994 Mastrototaro
5,320,715 A 6/1994 Berg
5,320,725 A 6/1994 Gregg et al.
5,322,063 A 6/1994 Allen et al.
5,330,634 A 7/1994 Wong et al.
5,340,722 A 8/1994 Wolfbeis et al.
5,342,789 A 8/1994 Chick et al.
5,356,786 A 10/1994 Heller et al.
5,360,404 A 11/1994 Novacek et al.
5,372,427 A 12/1994 Padovani et al.
5,379,238 A 1/1995 Stark
5,384,547 A 1/1995 Lynk et al.
5,390,671 A 2/1995 Lord et al.
5,391,250 A 2/1995 Cheney, II et al.
5,394,877 A 3/1995 Orr et al.
5,402,780 A 4/1995 Faasse, Jr.
5,408,999 A 4/1995 Singh et al.
5,410,326 A 4/1995 Goldstein
5,411,647 A 5/1995 Johnson et al.
5,431,160 A 7/1995 Wilkins
5,431,921 A 7/1995 Thombre
5,438,983 A 8/1995 Falcone
5,462,645 A 10/1995 Albery et al.
5,472,317 A 12/1995 Field et al.
5,482,473 A 1/1996 Lord et al.
5,489,414 A 2/1996 Schreiber et al.
5,497,772 A 3/1996 Schulman et al.
5,505,828 A 4/1996 Wong et al.
5,507,288 A 4/1996 Bocker et al.
5,509,410 A 4/1996 Hill et al.
5,514,718 A 5/1996 Lewis et al.
5,531,878 A 7/1996 Vadgama et al.
5,532,686 A 7/1996 Urbas et al.
5,543,326 A 8/1996 Heller et al.
5,552,997 A 9/1996 Massart
5,555,190 A 9/1996 Derby et al.
5,564,434 A 10/1996 Halperin et al.
5,568,806 A 10/1996 Cheney, II et al.
5,569,186 A 10/1996 Lord et al.
5,582,184 A 12/1996 Erickson et al.
5,586,553 A 12/1996 Halili et al.
5,593,852 A 1/1997 Heller et al.
5,601,435 A 2/1997 Quy
5,609,575 A 3/1997 Larson et al.
5,628,310 A 5/1997 Rao et al.
5,628,890 A 5/1997 Carter et al.
5,634,468 A 6/1997 Platt et al.
5,640,954 A 6/1997 Pfeiffer et al.
5,653,239 A 8/1997 Pompei et al.
5,660,163 A 8/1997 Schulman et al.
5,665,222 A 9/1997 Heller et al.
5,690,119 A 11/1997 Rytky et al.
5,707,502 A 1/1998 McCaffrey et al.
5,711,001 A 1/1998 Bussan et al.
5,711,861 A 1/1998 Ward et al.
5,724,030 A 3/1998 Urbas et al.
5,726,646 A 3/1998 Bane et al.
5,735,285 A 4/1998 Albert et al.
5,748,103 A 5/1998 Flach et al.
5,749,907 A 5/1998 Mann
5,772,586 A 6/1998 Heinonen et al.
5,791,344 A 8/1998 Schulman et al.
5,794,219 A 8/1998 Brown
5,804,047 A 9/1998 Karube et al.
5,807,375 A 9/1998 Gross et al.
5,820,551 A 10/1998 Hill et al.
5,822,715 A 10/1998 Worthington et al.
5,875,186 A 2/1999 Belanger et al.
5,891,049 A 4/1999 Cyrus et al.
5,899,855 A 5/1999 Brown
5,914,026 A 6/1999 Blubaugh, Jr. et al.
5,918,603 A 7/1999 Brown
5,919,141 A 7/1999 Money et al.
5,925,021 A 7/1999 Castellano et al.
5,942,979 A 8/1999 Luppino
5,951,485 A 9/1999 Cyrus et al.
5,951,521 A 9/1999 Mastrototaro et al.
5,957,854 A 9/1999 Besson et al.
5,959,529 A 9/1999 Kail, IV
5,961,451 A 10/1999 Reber et al.
5,964,993 A 10/1999 Blubaugh, Jr. et al.
5,965,380 A 10/1999 Heller et al.
5,971,922 A 10/1999 Arita et al.
5,987,353 A 11/1999 Khatchatrian et al.
5,995,860 A 11/1999 Sun et al.
6,001,067 A 12/1999 Shults et al.

(56) References Cited

U.S. PATENT DOCUMENTS 6,002,344 A 12/1999 Bandy et al.
6,004,278 A 12/1999 Botich et al.
6,022,315 A 2/2000 Iliff
6,024,699 A 2/2000 Surwit et al.
6,028,413 A 2/2000 Brockmann
6,031,454 A 2/2000 Lovejoy et al.
6,049,727 A 4/2000 Crothall
6,052,565 A 4/2000 Ishikura et al.
6,066,243 A 5/2000 Anderson et al.
6,071,391 A 6/2000 Gotoh et al.
6,083,710 A 7/2000 Heller et al.
6,088,608 A 7/2000 Schulman et al.
6,091,975 A 7/2000 Daddona et al.
6,091,976 A 7/2000 Pfeiffer et al.
6,091,987 A 7/2000 Thompson
6,093,172 A 7/2000 Funderburk et al.
6,096,268 A 8/2000 Inbar
6,096,364 A 8/2000 Bok et al.
6,103,033 A 8/2000 Say et al.
6,115,622 A 9/2000 Minoz
6,117,290 A 9/2000 Say et al.
6,119,028 A 9/2000 Schulman et al.
6,120,676 A 9/2000 Heller et al.
6,121,009 A 9/2000 Heller et al.
6,121,611 A 9/2000 Lindsay et al.
6,122,351 A 9/2000 Schlueter, Jr. et al.
6,129,823 A 10/2000 Hughes et al.
6,130,623 A 10/2000 MacLellan et al.
6,134,461 A 10/2000 Say et al.
6,141,573 A 10/2000 Kurnik et al.
6,143,164 A 11/2000 Heller et al.
6,144,837 A 11/2000 Quy
6,144,871 A 11/2000 Saito et al.
6,157,850 A 12/2000 Diab et al.
6,159,147 A 12/2000 Lichter et al.
6,159,181 A 12/2000 Crossman et al.
6,161,095 A 12/2000 Brown
6,162,611 A 12/2000 Heller et al.
6,167,362 A 12/2000 Brown
6,175,752 B1 1/2001 Say et al.
6,200,265 B1 3/2001 Walsh et al.
6,212,416 B1 4/2001 Ward et al.
6,219,574 B1 4/2001 Cormier et al.
6,223,283 B1 4/2001 Chaiken et al.
6,248,065 B1 6/2001 Brown
6,248,067 B1 6/2001 Causey, III et al.
6,254,586 B1 7/2001 Mann et al.
6,266,551 B1 7/2001 Osadchy et al.
6,270,455 B1 8/2001 Brown
6,275,717 B1 8/2001 Gross et al.
6,283,761 B1 9/2001 Joao
6,284,478 B1 9/2001 Heller et al.
6,291,200 B1 9/2001 LeJeune et al.
6,293,925 B1 9/2001 Safabash et al.
6,294,997 B1 9/2001 Paratore et al.
6,295,506 B1 9/2001 Heinonen et al.
6,298,255 B1 10/2001 Cordero et al.
6,299,757 B1 10/2001 Feldman et al.
6,306,104 B1 10/2001 Cunningham et al.
6,309,884 B1 10/2001 Cooper et al.
6,314,317 B1 11/2001 Willis
6,329,161 B1 12/2001 Heller et al.
6,338,790 B1 1/2002 Feldman et al.
6,348,640 B1 2/2002 Navot et al.
6,359,270 B1 3/2002 Bridson
6,359,444 B1 3/2002 Grimes
6,360,888 B1 3/2002 McIvor et al.
6,366,794 B1 4/2002 Moussy et al.
6,368,273 B1 4/2002 Brown
6,377,828 B1 4/2002 Chaiken et al.
6,377,894 B1 4/2002 Deweese et al.
6,379,301 B1 4/2002 Worthington et al.
6,387,048 B1 5/2002 Schulman et al.
6,400,974 B1 6/2002 Lesho
6,405,066 B1 6/2002 Essenpreis et al.
6,413,393 B1 7/2002 Van Antwerp et al.
6,416,471 B1 7/2002 Kumar et al.
6,418,332 B1 7/2002 Mastrototaro et al.
6,418,346 B1 7/2002 Nelson et al.
6,424,847 B1 7/2002 Mastrototaro et al.
6,427,088 B1 7/2002 Bowman, IV et al.
6,437,692 B1 8/2002 Petite et al.
6,440,068 B1 8/2002 Brown et al.
6,442,432 B2 8/2002 Lee
6,461,496 B1 10/2002 Feldman et al.
6,471,689 B1 10/2002 Joseph et al.
6,478,736 B1 11/2002 Mault
6,484,045 B1 11/2002 Holker et al.
6,484,046 B1 11/2002 Say et al.
6,493,069 B1 12/2002 Nagashimada et al.
6,496,729 B2 12/2002 Thompson
6,497,655 B1 12/2002 Linberg et al.
6,498,043 B1 12/2002 Schulman et al.
6,503,381 B1 1/2003 Gotoh et al.
6,514,460 B1 2/2003 Fendrock
6,514,718 B2 2/2003 Heller et al.
6,520,326 B2 2/2003 McIvor et al.
6,540,891 B1 4/2003 Stewart et al.
6,546,268 B1 4/2003 Ishikawa et al.
6,549,796 B2 4/2003 Sohrab
6,551,494 B1 4/2003 Heller et al.
6,554,798 B1 4/2003 Mann et al.
6,558,320 B1 5/2003 Causey, III et al.
6,558,321 B1 5/2003 Burd et al.
6,558,351 B1 5/2003 Steil et al.
6,560,471 B1 5/2003 Heller et al.
6,561,975 B1 5/2003 Pool et al.
6,561,978 B1 5/2003 Conn et al.
6,562,001 B2 5/2003 Lebel et al.
6,564,105 B2 5/2003 Starkweather et al.
6,565,509 B1 5/2003 Say et al.
6,571,128 B2 5/2003 Lebel et al.
6,572,542 B1 6/2003 Houben et al.
6,574,490 B2 6/2003 Abbink et al.
6,574,510 B2 6/2003 Von Arx et al.
6,576,101 B1 6/2003 Heller et al.
6,577,899 B2 6/2003 Lebel et al.
6,579,231 B1 6/2003 Phipps
6,579,690 B1 6/2003 Bonnecaze et al.
6,585,644 B2 7/2003 Lebel et al.
6,591,125 B1 7/2003 Buse et al.
6,592,745 B1 7/2003 Feldman et al.
6,595,919 B2 7/2003 Berner et al.
6,595,929 B2 7/2003 Stivoric et al.
6,600,997 B2 7/2003 Deweese et al.
6,605,200 B1 8/2003 Mao et al.
6,605,201 B1 8/2003 Mao et al.
6,607,509 B2 8/2003 Bobroff et al.
6,610,012 B2 8/2003 Mault
6,616,819 B1 9/2003 Liamos et al.
6,618,934 B1 9/2003 Feldman et al.
6,631,281 B1 10/2003 Kastle
6,633,772 B2 10/2003 Ford et al.
6,635,014 B2 10/2003 Starkweather et al.
6,635,167 B1 10/2003 Batman et al.
6,638,772 B1 10/2003 Douglas et al.
6,641,533 B2 11/2003 Causey, III et al.
6,648,821 B2 11/2003 Lebel et al.
6,650,471 B2 11/2003 Doi
6,654,625 B1 11/2003 Say et al.
6,656,114 B1 12/2003 Poulson et al.
6,658,396 B1 12/2003 Tang et al.
6,659,948 B2 12/2003 Lebel et al.
6,668,196 B1 12/2003 Villegas et al.
6,676,816 B2 1/2004 Mao et al.
6,687,546 B2 2/2004 Lebel et al.
6,689,056 B1 2/2004 Kilcoyne et al.
6,694,191 B2 2/2004 Starkweather et al.
6,695,860 B1 2/2004 Ward et al.
6,702,857 B2 3/2004 Brauker et al.
6,720,887 B1 4/2004 Zunti
6,721,582 B2 4/2004 Trepagnier et al.
6,730,025 B1 5/2004 Platt
6,730,200 B1 5/2004 Stewart et al.

(56) References Cited

U.S. PATENT DOCUMENTS

| | | | |
|---|---|---|---|
| 6,731,976 | B2 | 5/2004 | Penn et al. |
| 6,733,446 | B2 | 5/2004 | Lebel et al. |
| 6,735,183 | B2 | 5/2004 | O'Toole et al. |
| 6,736,957 | B1 | 5/2004 | Forrow et al. |
| 6,740,075 | B2 | 5/2004 | Lebel et al. |
| 6,741,877 | B1 | 5/2004 | Shults et al. |
| 6,743,635 | B2 | 6/2004 | Neel et al. |
| 6,746,582 | B2 | 6/2004 | Heller et al. |
| 6,749,740 | B2 | 6/2004 | Liamos et al. |
| 6,758,810 | B2 | 7/2004 | Lebel et al. |
| 6,764,581 | B1 | 7/2004 | Forrow et al. |
| 6,770,030 | B1 | 8/2004 | Schaupp et al. |
| 6,773,671 | B1 | 8/2004 | Lewis et al. |
| 6,789,195 | B1 | 9/2004 | Prihoda et al. |
| 6,790,178 | B1 | 9/2004 | Mault et al. |
| 6,804,558 | B2 | 10/2004 | Haller et al. |
| 6,809,653 | B1 | 10/2004 | Mann et al. |
| 6,810,290 | B2 | 10/2004 | Lebel et al. |
| 6,811,533 | B2 | 11/2004 | Lebel et al. |
| 6,811,534 | B2 | 11/2004 | Bowman, IV et al. |
| 6,813,519 | B2 | 11/2004 | Lebel et al. |
| 6,837,858 | B2 | 1/2005 | Cunningham et al. |
| 6,850,790 | B2 | 2/2005 | Berner et al. |
| 6,862,465 | B2 | 3/2005 | Shults et al. |
| 6,873,268 | B2 | 3/2005 | Lebel et al. |
| 6,878,112 | B2 | 4/2005 | Linberg et al. |
| 6,881,551 | B2 | 4/2005 | Heller et al. |
| 6,892,085 | B2 | 5/2005 | McIvor et al. |
| 6,893,545 | B2 | 5/2005 | Gotoh et al. |
| 6,895,263 | B2 | 5/2005 | Shin et al. |
| 6,895,265 | B2 | 5/2005 | Silver |
| 6,912,413 | B2 | 6/2005 | Rantala et al. |
| 6,923,763 | B1 | 8/2005 | Kovatchev et al. |
| 6,923,764 | B2 | 8/2005 | Aceti et al. |
| 6,931,327 | B2 | 8/2005 | Goode, Jr. et al. |
| 6,932,892 | B2 | 8/2005 | Chen et al. |
| 6,932,894 | B2 | 8/2005 | Mao et al. |
| 6,936,006 | B2 | 8/2005 | Sabra |
| 6,940,403 | B2 | 9/2005 | Kail, IV |
| 6,941,163 | B2 | 9/2005 | Ford et al. |
| 6,942,518 | B2 | 9/2005 | Liamos et al. |
| 6,950,708 | B2 | 9/2005 | Bowman IV et al. |
| 6,954,662 | B2 | 10/2005 | Freger et al. |
| 6,958,705 | B2 | 10/2005 | Lebel et al. |
| 6,968,294 | B2 | 11/2005 | Gutta et al. |
| 6,968,375 | B1 | 11/2005 | Brown |
| 6,971,274 | B2 | 12/2005 | Olin |
| 6,974,437 | B2 | 12/2005 | Lebel et al. |
| 6,978,182 | B2 | 12/2005 | Mazar et al. |
| 6,987,965 | B2 | 1/2006 | Ng et al. |
| 6,989,750 | B2 | 1/2006 | Shanks et al. |
| 6,990,366 | B2 | 1/2006 | Say et al. |
| 6,997,907 | B2 | 2/2006 | Safabash et al. |
| 6,998,247 | B2 | 2/2006 | Monfre et al. |
| 6,999,854 | B2 | 2/2006 | Roth |
| 7,003,336 | B2 | 2/2006 | Holker et al. |
| 7,003,340 | B2 | 2/2006 | Say et al. |
| 7,003,341 | B2 | 2/2006 | Say et al. |
| 7,009,511 | B2 | 3/2006 | Mazar et al. |
| 7,011,630 | B2 | 3/2006 | Desai et al. |
| 7,015,817 | B2 | 3/2006 | Copley et al. |
| 7,016,713 | B2 | 3/2006 | Gardner et al. |
| 7,020,508 | B2 | 3/2006 | Stivoric et al. |
| 7,022,219 | B2 | 4/2006 | Mansouri et al. |
| 7,024,236 | B2 | 4/2006 | Ford et al. |
| 7,024,245 | B2 | 4/2006 | Lebel et al. |
| 7,025,774 | B2 | 4/2006 | Freeman et al. |
| 7,027,848 | B2 | 4/2006 | Robinson et al. |
| 7,027,931 | B1 | 4/2006 | Jones et al. |
| 7,029,444 | B2 | 4/2006 | Shin et al. |
| 7,041,068 | B2 | 5/2006 | Freeman et al. |
| 7,041,468 | B2 | 5/2006 | Drucker et al. |
| 7,043,287 | B1 | 5/2006 | Khalil et al. |
| 7,043,305 | B2 | 5/2006 | KenKnight et al. |
| 7,046,153 | B2 | 5/2006 | Oja et al. |
| 7,052,472 | B1 | 5/2006 | Miller et al. |
| 7,052,483 | B2 | 5/2006 | Wojcik |
| 7,056,302 | B2 | 6/2006 | Douglas |
| 7,058,453 | B2 | 6/2006 | Nelson et al. |
| 7,060,031 | B2 | 6/2006 | Webb et al. |
| 7,074,307 | B2 | 7/2006 | Simpson et al. |
| 7,081,195 | B2 | 7/2006 | Simpson et al. |
| 7,082,334 | B2 | 7/2006 | Boute et al. |
| 7,092,891 | B2 | 8/2006 | Maus et al. |
| 7,098,803 | B2 | 8/2006 | Mann et al. |
| 7,108,778 | B2 | 9/2006 | Simpson et al. |
| 7,110,803 | B2 | 9/2006 | Shults et al. |
| 7,113,821 | B1 | 9/2006 | Sun et al. |
| 7,118,667 | B2 | 10/2006 | Lee |
| 7,123,950 | B2 | 10/2006 | Mannheimer |
| 7,125,382 | B2 | 10/2006 | Zhou et al. |
| 7,134,999 | B2 | 11/2006 | Brauker et al. |
| 7,136,689 | B2 | 11/2006 | Shults et al. |
| 7,148,803 | B2 | 12/2006 | Bandy et al. |
| 7,153,265 | B2 | 12/2006 | Vachon |
| 7,155,290 | B2 | 12/2006 | Von Arx et al. |
| 7,155,729 | B1 | 12/2006 | Andrew et al. |
| 7,167,818 | B2 | 1/2007 | Brown |
| 7,171,274 | B2 | 1/2007 | Starkweather et al. |
| 7,179,226 | B2 | 2/2007 | Crothall et al. |
| 7,183,102 | B2 | 2/2007 | Monfre et al. |
| 7,190,988 | B2 | 3/2007 | Say et al. |
| 7,192,450 | B2 | 3/2007 | Brauker et al. |
| 7,198,606 | B2 | 4/2007 | Boecker et al. |
| 7,203,549 | B2 | 4/2007 | Schommer et al. |
| 7,207,974 | B2 | 4/2007 | Safabash et al. |
| 7,223,236 | B2 | 5/2007 | Brown |
| 7,225,535 | B2 | 6/2007 | Feldman et al. |
| 7,226,442 | B2 | 6/2007 | Sheppard et al. |
| 7,226,978 | B2 | 6/2007 | Tapsak et al. |
| 7,228,182 | B2 | 6/2007 | Healy et al. |
| 7,237,712 | B2 | 7/2007 | DeRocco et al. |
| 7,242,294 | B2 | 7/2007 | Warrior et al. |
| 7,258,666 | B2 | 8/2007 | Brown |
| 7,276,029 | B2 | 10/2007 | Goode, Jr. et al. |
| 7,278,983 | B2 | 10/2007 | Ireland et al. |
| 7,286,894 | B1 | 10/2007 | Grant et al. |
| 7,299,082 | B2 | 11/2007 | Feldman et al. |
| 7,301,463 | B1 | 11/2007 | Paterno |
| 7,310,544 | B2 | 12/2007 | Brister et al. |
| 7,315,739 | B2 | 1/2008 | Burch et al. |
| 7,318,816 | B2 | 1/2008 | Bobroff et al. |
| 7,324,012 | B2 | 1/2008 | Mann et al. |
| 7,324,850 | B2 | 1/2008 | Persen et al. |
| 7,329,239 | B2 | 2/2008 | Safabash et al. |
| 7,335,294 | B2 | 2/2008 | Heller et al. |
| 7,347,819 | B2 | 3/2008 | Lebel et al. |
| 7,354,420 | B2 | 4/2008 | Steil et al. |
| 7,364,592 | B2 | 4/2008 | Carr-Brendel et al. |
| 7,366,556 | B2 | 4/2008 | Brister et al. |
| 7,379,765 | B2 | 5/2008 | Petisce et al. |
| 7,381,184 | B2 | 6/2008 | Funderburk et al. |
| 7,384,397 | B2 | 6/2008 | Zhang et al. |
| 7,387,010 | B2 | 6/2008 | Sunshine et al. |
| 7,392,167 | B2 | 6/2008 | Brown |
| 7,399,277 | B2 | 7/2008 | Saidara et al. |
| 7,402,153 | B2 | 7/2008 | Steil et al. |
| 7,404,796 | B2 | 7/2008 | Ginsberg |
| 7,406,105 | B2 | 7/2008 | Delmain et al. |
| 7,419,573 | B2 | 9/2008 | Gundel |
| 7,424,318 | B2 | 9/2008 | Brister et al. |
| 7,429,258 | B2 | 9/2008 | Angel et al. |
| 7,455,663 | B2 | 11/2008 | Bikovsky |
| 7,460,898 | B2 | 12/2008 | Brister et al. |
| 7,462,264 | B2 | 12/2008 | Heller et al. |
| 7,467,003 | B2 | 12/2008 | Brister et al. |
| 7,468,125 | B2 | 12/2008 | Kraft et al. |
| 7,471,972 | B2 | 12/2008 | Rhodes et al. |
| 7,492,254 | B2 | 2/2009 | Bandy et al. |
| 7,494,465 | B2 | 2/2009 | Brister et al. |
| 7,497,827 | B2 | 3/2009 | Brister et al. |
| 7,499,002 | B2 | 3/2009 | Blasko et al. |
| 7,501,053 | B2 | 3/2009 | Karinka et al. |
| 7,519,408 | B2 | 4/2009 | Rasdal et al. |

(56) References Cited

U.S. PATENT DOCUMENTS

| | | | |
|---|---|---|---|
| 7,519,478 | B2 | 4/2009 | Bartkowiak et al. |
| 7,523,004 | B2 | 4/2009 | Bartkowiak et al. |
| 7,565,197 | B2 | 7/2009 | Haubrich et al. |
| 7,574,266 | B2 | 8/2009 | Dudding et al. |
| 7,583,990 | B2 | 9/2009 | Goode, Jr. et al. |
| 7,591,801 | B2 | 9/2009 | Brauker et al. |
| 7,599,726 | B2 | 10/2009 | Goode, Jr. et al. |
| 7,602,310 | B2 | 10/2009 | Mann et al. |
| 7,604,178 | B2 | 10/2009 | Stewart |
| 7,613,491 | B2 | 11/2009 | Boock et al. |
| 7,615,007 | B2 | 11/2009 | Shults et al. |
| 7,618,369 | B2 | 11/2009 | Hayter et al. |
| 7,624,028 | B1 | 11/2009 | Brown |
| 7,630,748 | B2 | 12/2009 | Budiman |
| 7,632,228 | B2 | 12/2009 | Brauker et al. |
| 7,635,594 | B2 | 12/2009 | Holmes et al. |
| 7,637,868 | B2 | 12/2009 | Saint et al. |
| 7,640,048 | B2 | 12/2009 | Dobbles et al. |
| 7,643,798 | B2 | 1/2010 | Ljung |
| 7,643,971 | B2 | 1/2010 | Brown |
| 7,651,596 | B2 | 1/2010 | Petisce et al. |
| 7,651,845 | B2 | 1/2010 | Doyle, III et al. |
| 7,653,425 | B2 | 1/2010 | Hayter et al. |
| 7,654,956 | B2 | 2/2010 | Brister et al. |
| 7,657,297 | B2 | 2/2010 | Simpson et al. |
| 7,659,823 | B1 | 2/2010 | Killian et al. |
| 7,668,596 | B2 | 2/2010 | Von Arx et al. |
| 7,684,999 | B2 | 3/2010 | Brown |
| 7,689,440 | B2 | 3/2010 | Brown |
| 7,693,485 | B2 | 4/2010 | Parys |
| 7,697,967 | B2 | 4/2010 | Stafford |
| 7,699,775 | B2 | 4/2010 | Desai et al. |
| 7,711,402 | B2 | 5/2010 | Shults et al. |
| 7,711,493 | B2 | 5/2010 | Bartkowiak et al. |
| 7,713,574 | B2 | 5/2010 | Brister et al. |
| 7,715,893 | B2 | 5/2010 | Kamath et al. |
| 7,727,147 | B1 | 6/2010 | Osorio et al. |
| 7,731,657 | B2 | 6/2010 | Stafford |
| 7,736,310 | B2 | 6/2010 | Taub |
| 7,736,344 | B2 | 6/2010 | Moberg et al. |
| 7,741,734 | B2 | 6/2010 | Joannopoulos et al. |
| 7,751,864 | B2 | 7/2010 | Buck, Jr. |
| 7,754,093 | B2 | 7/2010 | Forrow et al. |
| 7,763,042 | B2 | 7/2010 | Iio et al. |
| 7,766,829 | B2 | 8/2010 | Sloan et al. |
| 7,768,387 | B2 | 8/2010 | Fennell et al. |
| 7,768,408 | B2 | 8/2010 | Reggiardo et al. |
| 7,771,352 | B2 | 8/2010 | Shults et al. |
| 7,778,680 | B2 | 8/2010 | Goode et al. |
| 7,779,332 | B2 | 8/2010 | Karr et al. |
| 7,782,192 | B2 | 8/2010 | Jeckelmann et al. |
| 7,783,333 | B2 | 8/2010 | Brister et al. |
| 7,791,467 | B2 | 9/2010 | Mazar et al. |
| 7,792,562 | B2 | 9/2010 | Shults et al. |
| 7,797,367 | B1 | 9/2010 | Gelvin et al. |
| 7,811,231 | B2 | 10/2010 | Jin et al. |
| 7,813,809 | B2 | 10/2010 | Strother et al. |
| 7,822,454 | B1 | 10/2010 | Alden et al. |
| 7,831,310 | B2 | 11/2010 | Lebel et al. |
| 7,857,760 | B2 | 12/2010 | Brister et al. |
| 7,860,574 | B2 | 12/2010 | Von Arx et al. |
| 7,866,026 | B1 | 1/2011 | Wang et al. |
| 7,873,595 | B2 | 1/2011 | Singh et al. |
| 7,877,274 | B2 | 1/2011 | Brown |
| 7,877,276 | B2 | 1/2011 | Brown |
| 7,882,611 | B2 | 2/2011 | Shah et al. |
| 7,885,697 | B2 | 2/2011 | Brister et al. |
| 7,889,069 | B2 | 2/2011 | Fifolt et al. |
| 7,899,511 | B2 | 3/2011 | Shults et al. |
| 7,899,545 | B2 | 3/2011 | John |
| 7,912,674 | B2 | 3/2011 | Killoren Clark et al. |
| 7,914,460 | B2 | 3/2011 | Melker et al. |
| 7,916,013 | B2 | 3/2011 | Stevenson |
| 7,921,186 | B2 | 4/2011 | Brown |
| 7,937,255 | B2 | 5/2011 | Brown |
| 7,938,797 | B2 | 5/2011 | Estes |
| 7,941,200 | B2 | 5/2011 | Weinert et al. |
| 7,941,308 | B2 | 5/2011 | Brown |
| 7,941,323 | B2 | 5/2011 | Brown |
| 7,941,326 | B2 | 5/2011 | Brown |
| 7,941,327 | B2 | 5/2011 | Brown |
| 7,946,984 | B2 | 5/2011 | Brister et al. |
| 7,946,985 | B2 | 5/2011 | Mastrototaro et al. |
| 7,949,507 | B2 | 5/2011 | Brown |
| 7,955,258 | B2 | 6/2011 | Goscha et al. |
| 7,966,230 | B2 | 6/2011 | Brown |
| 7,970,448 | B2 | 6/2011 | Shults et al. |
| 7,970,620 | B2 | 6/2011 | Brown |
| 7,972,267 | B2 | 7/2011 | Brown |
| 7,972,296 | B2 | 7/2011 | Braig et al. |
| 7,976,466 | B2 | 7/2011 | Ward et al. |
| 7,978,063 | B2 | 7/2011 | Baldus et al. |
| 7,979,259 | B2 | 7/2011 | Brown |
| 7,979,284 | B2 | 7/2011 | Brown |
| 7,996,158 | B2 | 8/2011 | Hayter et al. |
| 7,999,674 | B2 | 8/2011 | Kamen |
| 8,005,524 | B2 | 8/2011 | Brauker et al. |
| 8,010,174 | B2 | 8/2011 | Goode et al. |
| 8,010,256 | B2 | 8/2011 | Oowada |
| 8,015,025 | B2 | 9/2011 | Brown |
| 8,015,030 | B2 | 9/2011 | Brown |
| 8,015,033 | B2 | 9/2011 | Brown |
| 8,019,618 | B2 | 9/2011 | Brown |
| 8,024,201 | B2 | 9/2011 | Brown |
| 8,032,399 | B2 | 10/2011 | Brown |
| 8,060,173 | B2 | 11/2011 | Goode, Jr. et al. |
| 8,072,310 | B1 | 12/2011 | Everhart |
| 8,090,445 | B2 | 1/2012 | Ginggen |
| 8,093,991 | B2 | 1/2012 | Stevenson et al. |
| 8,094,009 | B2 | 1/2012 | Allen et al. |
| 8,098,159 | B2 | 1/2012 | Batra et al. |
| 8,098,160 | B2 | 1/2012 | Howarth et al. |
| 8,098,161 | B2 | 1/2012 | Lavedas |
| 8,098,201 | B2 | 1/2012 | Choi et al. |
| 8,098,208 | B2 | 1/2012 | Ficker et al. |
| 8,102,021 | B2 | 1/2012 | Degani |
| 8,102,154 | B2 | 1/2012 | Bishop et al. |
| 8,102,263 | B2 | 1/2012 | Yeo et al. |
| 8,102,789 | B2 | 1/2012 | Rosar et al. |
| 8,103,241 | B2 | 1/2012 | Young et al. |
| 8,103,325 | B2 | 1/2012 | Swedlow et al. |
| 8,103,471 | B2 | 1/2012 | Hayter |
| 8,111,042 | B2 | 2/2012 | Bennett |
| 8,115,488 | B2 | 2/2012 | McDowell |
| 8,116,681 | B2 | 2/2012 | Baarman |
| 8,116,683 | B2 | 2/2012 | Baarman |
| 8,116,837 | B2 | 2/2012 | Huang |
| 8,117,481 | B2 | 2/2012 | Anselmi et al. |
| 8,120,493 | B2 | 2/2012 | Burr |
| 8,124,452 | B2 | 2/2012 | Sheats |
| 8,130,093 | B2 | 3/2012 | Mazar et al. |
| 8,131,351 | B2 | 3/2012 | Kalgren et al. |
| 8,131,365 | B2 | 3/2012 | Zhang et al. |
| 8,131,565 | B2 | 3/2012 | Dicks et al. |
| 8,132,037 | B2 | 3/2012 | Fehr et al. |
| 8,135,352 | B2 | 3/2012 | Langsweirdt et al. |
| 8,136,735 | B2 | 3/2012 | Arai et al. |
| 8,138,925 | B2 | 3/2012 | Downie et al. |
| 8,140,160 | B2 | 3/2012 | Pless et al. |
| 8,140,168 | B2 | 3/2012 | Olson et al. |
| 8,140,299 | B2 | 3/2012 | Siess |
| 8,140,312 | B2 | 3/2012 | Hayter et al. |
| 8,150,321 | B2 | 4/2012 | Winter et al. |
| 8,150,516 | B2 | 4/2012 | Levine et al. |
| 8,160,900 | B2 | 4/2012 | Taub et al. |
| 8,170,803 | B2 | 5/2012 | Kamath et al. |
| 8,179,266 | B2 | 5/2012 | Hermle |
| 8,192,394 | B2 | 6/2012 | Estes et al. |
| 8,216,138 | B1 | 7/2012 | McGarraugh et al. |
| 8,239,166 | B2 | 8/2012 | Hayter et al. |
| 8,255,026 | B1 | 8/2012 | Al-Ali |
| 8,260,558 | B2 | 9/2012 | Hayter et al. |
| 8,282,549 | B2 | 10/2012 | Brauker et al. |
| 8,374,668 | B1 | 2/2013 | Hayter et al. |

(56) References Cited

U.S. PATENT DOCUMENTS

| | | | |
|---|---|---|---|
| 8,376,945 | B2 | 2/2013 | Hayter et al. |
| 8,377,271 | B2 | 2/2013 | Mao et al. |
| 8,401,194 | B2 | 3/2013 | Nierzwick et al. |
| 8,409,093 | B2 | 4/2013 | Bugler |
| 8,444,560 | B2 | 5/2013 | Hayter et al. |
| 8,457,703 | B2 | 6/2013 | Al-Ali |
| 8,461,985 | B2 | 6/2013 | Fennell et al. |
| 8,484,005 | B2 | 7/2013 | Hayter et al. |
| 8,532,935 | B2 | 9/2013 | Budiman |
| 8,543,354 | B2 | 9/2013 | Luo et al. |
| 8,560,038 | B2 | 10/2013 | Hayter et al. |
| 8,571,808 | B2 | 10/2013 | Hayter |
| 8,583,205 | B2 | 11/2013 | Budiman et al. |
| 8,597,188 | B2 | 12/2013 | Bernstein et al. |
| 8,597,570 | B2 | 12/2013 | Terashima et al. |
| 8,600,681 | B2 | 12/2013 | Hayter et al. |
| 8,612,163 | B2 | 12/2013 | Hayter et al. |
| 8,657,746 | B2 | 2/2014 | Roy |
| 8,682,615 | B2 | 3/2014 | Hayter et al. |
| 8,710,993 | B2 | 4/2014 | Hayter et al. |
| 8,834,366 | B2 | 9/2014 | Hayter et al. |
| 8,845,536 | B2 | 9/2014 | Brauker et al. |
| 8,924,159 | B2 | 12/2014 | Taub et al. |
| 9,000,914 | B2 | 4/2015 | Baker et al. |
| 9,060,719 | B2 | 6/2015 | Hayter et al. |
| 9,211,065 | B2 | 12/2015 | Marsh et al. |
| 9,289,179 | B2 | 3/2016 | Hayter et al. |
| 9,344,777 | B2 | 5/2016 | He et al. |
| 9,398,872 | B2 | 7/2016 | Hayter et al. |
| 9,408,566 | B2 | 8/2016 | Hayter et al. |
| 9,439,586 | B2 | 9/2016 | Bugler |
| 9,483,608 | B2 | 11/2016 | Hayter et al. |
| 9,558,325 | B2 | 1/2017 | Hayter et al. |
| 9,743,872 | B2 | 8/2017 | Hayter et al. |
| 9,801,541 | B2 | 10/2017 | Mensinger et al. |
| 9,913,600 | B2 | 3/2018 | Taub et al. |
| 9,980,140 | B1 | 5/2018 | Spencer et al. |
| 10,375,222 | B2 | 8/2019 | Mandapaka et al. |
| 10,855,788 | B2 | 12/2020 | Arabo et al. |
| 10,856,785 | B2 | 12/2020 | Taub et al. |
| 11,213,204 | B2 | 1/2022 | Mensinger et al. |
| 11,264,133 | B2 | 3/2022 | Bernstein et al. |
| 11,563,812 | B2 | 1/2023 | Sloan et al. |
| 11,678,821 | B2 | 6/2023 | Taub et al. |
| 11,991,175 | B2 | 5/2024 | Rolfe et al. |
| 2001/0011224 | A1 | 8/2001 | Brown |
| 2001/0020124 | A1 | 9/2001 | Tamada |
| 2001/0037060 | A1 | 11/2001 | Thompson et al. |
| 2001/0037366 | A1 | 11/2001 | Webb et al. |
| 2001/0047604 | A1 | 12/2001 | Valiulis |
| 2002/0016534 | A1 | 2/2002 | Trepagnier et al. |
| 2002/0016568 | A1 | 2/2002 | Lebel et al. |
| 2002/0019022 | A1 | 2/2002 | Dunn et al. |
| 2002/0042090 | A1 | 4/2002 | Heller et al. |
| 2002/0054320 | A1 | 5/2002 | Ogino |
| 2002/0065454 | A1 | 5/2002 | Lebel et al. |
| 2002/0072784 | A1 | 6/2002 | Sheppard et al. |
| 2002/0095076 | A1 | 7/2002 | Krausman et al. |
| 2002/0103499 | A1 | 8/2002 | Perez et al. |
| 2002/0106709 | A1 | 8/2002 | Potts et al. |
| 2002/0109621 | A1 | 8/2002 | Khair et al. |
| 2002/0111832 | A1 | 8/2002 | Judge |
| 2002/0117639 | A1 | 8/2002 | Paolini et al. |
| 2002/0120186 | A1 | 8/2002 | Keimel |
| 2002/0128594 | A1 | 9/2002 | Das et al. |
| 2002/0133107 | A1 | 9/2002 | Darcey |
| 2002/0147135 | A1 | 10/2002 | Schnell |
| 2002/0150959 | A1 | 10/2002 | Lejeunne et al. |
| 2002/0161288 | A1 | 10/2002 | Shin et al. |
| 2002/0165443 | A1 | 11/2002 | Mori |
| 2002/0178126 | A1 | 11/2002 | Beck et al. |
| 2002/0188748 | A1 | 12/2002 | Blackwell et al. |
| 2003/0005464 | A1 | 1/2003 | Gropper et al. |
| 2003/0021729 | A1 | 1/2003 | Moller et al. |
| 2003/0023317 | A1 | 1/2003 | Brauker et al. |

| | | | |
|---|---|---|---|
| 2003/0023461 | A1 | 1/2003 | Quintanilla et al. |
| 2003/0028089 | A1 | 2/2003 | Galley et al. |
| 2003/0032077 | A1 | 2/2003 | Itoh et al. |
| 2003/0032867 | A1 | 2/2003 | Crothall et al. |
| 2003/0032874 | A1 | 2/2003 | Rhodes et al. |
| 2003/0042137 | A1 | 3/2003 | Mao et al. |
| 2003/0050009 | A1 | 3/2003 | Kurisko et al. |
| 2003/0050546 | A1 | 3/2003 | Desai et al. |
| 2003/0054428 | A1 | 3/2003 | Monfre et al. |
| 2003/0060692 | A1 | 3/2003 | Ruchti et al. |
| 2003/0060753 | A1 | 3/2003 | Starkweather et al. |
| 2003/0065308 | A1 | 4/2003 | Lebel et al. |
| 2003/0065536 | A1 | 4/2003 | Hansen et al. |
| 2003/0100040 | A1 | 5/2003 | Bonnecaze et al. |
| 2003/0100821 | A1 | 5/2003 | Heller et al. |
| 2003/0114897 | A1 | 6/2003 | Von Arx et al. |
| 2003/0134347 | A1 | 7/2003 | Heller et al. |
| 2003/0144581 | A1 | 7/2003 | Conn et al. |
| 2003/0147515 | A1 | 8/2003 | Kai et al. |
| 2003/0153900 | A1 | 8/2003 | Aceti et al. |
| 2003/0163351 | A1 | 8/2003 | Brown |
| 2003/0168338 | A1 | 9/2003 | Gao et al. |
| 2003/0176933 | A1 | 9/2003 | Lebel et al. |
| 2003/0187338 | A1 | 10/2003 | Say et al. |
| 2003/0191377 | A1 | 10/2003 | Robinson et al. |
| 2003/0199744 | A1 | 10/2003 | Buse et al. |
| 2003/0199790 | A1 | 10/2003 | Boecker et al. |
| 2003/0208113 | A1 | 11/2003 | Mault et al. |
| 2003/0212379 | A1 | 11/2003 | Bylund et al. |
| 2003/0217966 | A1 | 11/2003 | Tapsak et al. |
| 2003/0229723 | A1 | 12/2003 | Kangas et al. |
| 2003/0235817 | A1 | 12/2003 | Bartkowiak et al. |
| 2004/0010186 | A1 | 1/2004 | Kimball et al. |
| 2004/0010207 | A1 | 1/2004 | Flaherty et al. |
| 2004/0011671 | A1 | 1/2004 | Shults et al. |
| 2004/0015102 | A1 | 1/2004 | Cummings et al. |
| 2004/0024553 | A1 | 2/2004 | Monfre et al. |
| 2004/0040840 | A1 | 3/2004 | Mao et al. |
| 2004/0041749 | A1 | 3/2004 | Dixon |
| 2004/0045879 | A1 | 3/2004 | Shults et al. |
| 2004/0054263 | A1 | 3/2004 | Moerman et al. |
| 2004/0060818 | A1 | 4/2004 | Feldman et al. |
| 2004/0063435 | A1 | 4/2004 | Sakamoto et al. |
| 2004/0064068 | A1 | 4/2004 | DeNuzzio et al. |
| 2004/0068230 | A1 | 4/2004 | Estes et al. |
| 2004/0073266 | A1 | 4/2004 | Haefner et al. |
| 2004/0078215 | A1 | 4/2004 | Dahlin et al. |
| 2004/0093167 | A1 | 5/2004 | Braig et al. |
| 2004/0099529 | A1 | 5/2004 | Mao et al. |
| 2004/0106858 | A1 | 6/2004 | Say et al. |
| 2004/0111017 | A1 | 6/2004 | Say et al. |
| 2004/0117204 | A1 | 6/2004 | Mazar et al. |
| 2004/0117210 | A1 | 6/2004 | Brown |
| 2004/0122353 | A1 | 6/2004 | Shahmirian et al. |
| 2004/0128225 | A1 | 7/2004 | Thompson et al. |
| 2004/0133164 | A1 | 7/2004 | Funderburk et al. |
| 2004/0133390 | A1 | 7/2004 | Osorio et al. |
| 2004/0135571 | A1 | 7/2004 | Uutela et al. |
| 2004/0135684 | A1 | 7/2004 | Steinthal et al. |
| 2004/0138588 | A1 | 7/2004 | Saikley et al. |
| 2004/0142403 | A1 | 7/2004 | Hetzel et al. |
| 2004/0147872 | A1 | 7/2004 | Thompson |
| 2004/0152622 | A1 | 8/2004 | Keith et al. |
| 2004/0162678 | A1 | 8/2004 | Hetzel et al. |
| 2004/0167801 | A1 | 8/2004 | Say et al. |
| 2004/0171921 | A1 | 9/2004 | Say et al. |
| 2004/0172307 | A1 | 9/2004 | Gruber |
| 2004/0176672 | A1 | 9/2004 | Silver et al. |
| 2004/0186362 | A1 | 9/2004 | Brauker et al. |
| 2004/0186365 | A1 | 9/2004 | Jin et al. |
| 2004/0193020 | A1 | 9/2004 | Chiba et al. |
| 2004/0193090 | A1 | 9/2004 | Lebel et al. |
| 2004/0199056 | A1 | 10/2004 | Husemann et al. |
| 2004/0199059 | A1 | 10/2004 | Brauker et al. |
| 2004/0204687 | A1 | 10/2004 | Mogensen et al. |
| 2004/0204868 | A1 | 10/2004 | Maynard et al. |
| 2004/0223985 | A1 | 11/2004 | Dunfiled et al. |
| 2004/0225338 | A1 | 11/2004 | Lebel et al. |
| 2004/0236200 | A1 | 11/2004 | Say et al. |

(56) References Cited

U.S. PATENT DOCUMENTS

| | | | |
|---|---|---|---|
| 2004/0249253 | A1 | 12/2004 | Racchini et al. |
| 2004/0254433 | A1 | 12/2004 | Bandis et al. |
| 2004/0254434 | A1 | 12/2004 | Goodnow et al. |
| 2004/0260478 | A1 | 12/2004 | Schwamm |
| 2004/0267300 | A1 | 12/2004 | Mace |
| 2005/0001024 | A1 | 1/2005 | Kusaka et al. |
| 2005/0003470 | A1 | 1/2005 | Nelson et al. |
| 2005/0004494 | A1 | 1/2005 | Perez et al. |
| 2005/0010269 | A1 | 1/2005 | Lebel et al. |
| 2005/0017864 | A1 | 1/2005 | Tsoukalis |
| 2005/0027177 | A1 | 2/2005 | Shin et al. |
| 2005/0027181 | A1 | 2/2005 | Goode et al. |
| 2005/0027182 | A1 | 2/2005 | Siddiqui et al. |
| 2005/0031689 | A1 | 2/2005 | Shults et al. |
| 2005/0038680 | A1 | 2/2005 | McMahon |
| 2005/0043598 | A1 | 2/2005 | Goode et al. |
| 2005/0049179 | A1 | 3/2005 | Davidson et al. |
| 2005/0049473 | A1 | 3/2005 | Desai et al. |
| 2005/0049501 | A1 | 3/2005 | Conero et al. |
| 2005/0060194 | A1 | 3/2005 | Brown |
| 2005/0070774 | A1 | 3/2005 | Addison et al. |
| 2005/0090607 | A1 | 4/2005 | Tapsak et al. |
| 2005/0096511 | A1 | 5/2005 | Fox et al. |
| 2005/0096516 | A1 | 5/2005 | Soykan et al. |
| 2005/0101912 | A1 | 5/2005 | Faust et al. |
| 2005/0112169 | A1 | 5/2005 | Brauker et al. |
| 2005/0113648 | A1 | 5/2005 | Yang et al. |
| 2005/0113886 | A1 | 5/2005 | Fischell et al. |
| 2005/0114068 | A1 | 5/2005 | Chey et al. |
| 2005/0115832 | A1 | 6/2005 | Simpson et al. |
| 2005/0116683 | A1 | 6/2005 | Cheng et al. |
| 2005/0121322 | A1 | 6/2005 | Say et al. |
| 2005/0131346 | A1 | 6/2005 | Douglas |
| 2005/0134731 | A1 | 6/2005 | Lee et al. |
| 2005/0137530 | A1 | 6/2005 | Campbell et al. |
| 2005/0143635 | A1 | 6/2005 | Kamath et al. |
| 2005/0148890 | A1 | 7/2005 | Hastings |
| 2005/0154271 | A1 | 7/2005 | Rasdal et al. |
| 2005/0173245 | A1 | 8/2005 | Feldman et al. |
| 2005/0176136 | A1 | 8/2005 | Burd et al. |
| 2005/0177398 | A1 | 8/2005 | Watanabe et al. |
| 2005/0182306 | A1 | 8/2005 | Sloan |
| 2005/0184153 | A1 | 8/2005 | Auchinleck |
| 2005/0187442 | A1 | 8/2005 | Cho et al. |
| 2005/0187720 | A1 | 8/2005 | Goode, Jr. et al. |
| 2005/0192557 | A1 | 9/2005 | Brauker et al. |
| 2005/0195930 | A1 | 9/2005 | Spital et al. |
| 2005/0196821 | A1 | 9/2005 | Monfre et al. |
| 2005/0197793 | A1 | 9/2005 | Baker |
| 2005/0199494 | A1 | 9/2005 | Say et al. |
| 2005/0203360 | A1 | 9/2005 | Brauker et al. |
| 2005/0204134 | A1 | 9/2005 | Von Arx et al. |
| 2005/0214892 | A1 | 9/2005 | Kovatchev et al. |
| 2005/0228883 | A1 | 10/2005 | Brown |
| 2005/0239154 | A1 | 10/2005 | Feldman et al. |
| 2005/0239156 | A1 | 10/2005 | Drucker et al. |
| 2005/0240245 | A1 | 10/2005 | Bange et al. |
| 2005/0241957 | A1 | 11/2005 | Mao et al. |
| 2005/0242479 | A1 | 11/2005 | Petisce et al. |
| 2005/0245795 | A1 | 11/2005 | Goode, Jr. et al. |
| 2005/0245799 | A1 | 11/2005 | Brauker et al. |
| 2005/0251033 | A1 | 11/2005 | Scarantino et al. |
| 2005/0261563 | A1 | 11/2005 | Zhou et al. |
| 2005/0277164 | A1 | 12/2005 | Drucker et al. |
| 2005/0277912 | A1 | 12/2005 | John |
| 2005/0283114 | A1 | 12/2005 | Bresina et al. |
| 2005/0287620 | A1 | 12/2005 | Heller et al. |
| 2006/0001538 | A1 | 1/2006 | Kraft et al. |
| 2006/0001551 | A1 | 1/2006 | Kraft et al. |
| 2006/0010014 | A1 | 1/2006 | Brown |
| 2006/0010098 | A1 | 1/2006 | Goodnow et al. |
| 2006/0015020 | A1 | 1/2006 | Neale et al. |
| 2006/0015024 | A1 | 1/2006 | Brister et al. |
| 2006/0016700 | A1 | 1/2006 | Brister et al. |
| 2006/0017923 | A1 | 1/2006 | Ruchti et al. |
| 2006/0019327 | A1 | 1/2006 | Brister et al. |
| 2006/0020186 | A1 | 1/2006 | Brister et al. |
| 2006/0020187 | A1 | 1/2006 | Brister et al. |
| 2006/0020188 | A1 | 1/2006 | Kamath et al. |
| 2006/0020189 | A1 | 1/2006 | Brister et al. |
| 2006/0020190 | A1 | 1/2006 | Kamath et al. |
| 2006/0020191 | A1 | 1/2006 | Brister et al. |
| 2006/0020192 | A1 | 1/2006 | Brister et al. |
| 2006/0020300 | A1 | 1/2006 | Nghiem et al. |
| 2006/0025662 | A1 | 2/2006 | Buse et al. |
| 2006/0025663 | A1 | 2/2006 | Talbot et al. |
| 2006/0031094 | A1 | 2/2006 | Cohen et al. |
| 2006/0036139 | A1 | 2/2006 | Brister et al. |
| 2006/0036140 | A1 | 2/2006 | Brister et al. |
| 2006/0036141 | A1 | 2/2006 | Kamath et al. |
| 2006/0036142 | A1 | 2/2006 | Brister et al. |
| 2006/0036143 | A1 | 2/2006 | Brister et al. |
| 2006/0036144 | A1 | 2/2006 | Brister et al. |
| 2006/0036145 | A1 | 2/2006 | Brister et al. |
| 2006/0058588 | A1 | 3/2006 | Zdeblick |
| 2006/0079740 | A1 | 4/2006 | Silver et al. |
| 2006/0081469 | A1 | 4/2006 | Lee |
| 2006/0091006 | A1 | 5/2006 | Wang et al. |
| 2006/0142651 | A1 | 6/2006 | Brister et al. |
| 2006/0154642 | A1 | 7/2006 | Scannell |
| 2006/0166629 | A1 | 7/2006 | Reggiardo |
| 2006/0173406 | A1 | 8/2006 | Hayes et al. |
| 2006/0173444 | A1 | 8/2006 | Choy et al. |
| 2006/0183984 | A1 | 8/2006 | Dobbles et al. |
| 2006/0189851 | A1 | 8/2006 | Tvig et al. |
| 2006/0189863 | A1 | 8/2006 | Peyser et al. |
| 2006/0193375 | A1 | 8/2006 | Lee et al. |
| 2006/0219576 | A1 | 10/2006 | Jina |
| 2006/0222566 | A1 | 10/2006 | Brauker et al. |
| 2006/0224141 | A1 | 10/2006 | Rush et al. |
| 2006/0226985 | A1 | 10/2006 | Goodnow et al. |
| 2006/0229512 | A1 | 10/2006 | Petisce et al. |
| 2006/0234202 | A1 | 10/2006 | Brown |
| 2006/0235722 | A1 | 10/2006 | Brown |
| 2006/0241975 | A1 | 10/2006 | Brown |
| 2006/0247508 | A1 | 11/2006 | Fennell |
| 2006/0247710 | A1 | 11/2006 | Goetz et al. |
| 2006/0247985 | A1 | 11/2006 | Liamos et al. |
| 2006/0258929 | A1 | 11/2006 | Goode et al. |
| 2006/0264785 | A1 | 11/2006 | Dring et al. |
| 2006/0272652 | A1 | 12/2006 | Stocker et al. |
| 2006/0281985 | A1 | 12/2006 | Ward et al. |
| 2006/0285660 | A1 | 12/2006 | Brown |
| 2006/0285736 | A1 | 12/2006 | Brown |
| 2006/0287691 | A1 | 12/2006 | Drew |
| 2006/0287889 | A1 | 12/2006 | Brown |
| 2006/0287931 | A1 | 12/2006 | Brown |
| 2006/0290496 | A1 | 12/2006 | Peeters et al. |
| 2006/0293607 | A1 | 12/2006 | Alt et al. |
| 2007/0010950 | A1 | 1/2007 | Abensour et al. |
| 2007/0011320 | A1 | 1/2007 | Brown |
| 2007/0016381 | A1 | 1/2007 | Kamath et al. |
| 2007/0016445 | A1 | 1/2007 | Brown |
| 2007/0017983 | A1 | 1/2007 | Frank et al. |
| 2007/0021984 | A1 | 1/2007 | Brown |
| 2007/0027381 | A1 | 2/2007 | Stafford |
| 2007/0027383 | A1 | 2/2007 | Peyser et al. |
| 2007/0027507 | A1 | 2/2007 | Burdett et al. |
| 2007/0032717 | A1 | 2/2007 | Brister et al. |
| 2007/0033074 | A1 | 2/2007 | Nitzan et al. |
| 2007/0038044 | A1 | 2/2007 | Dobbles et al. |
| 2007/0043279 | A1 | 2/2007 | Mannheimer et al. |
| 2007/0055799 | A1 | 3/2007 | Koehler et al. |
| 2007/0056858 | A1 | 3/2007 | Chen et al. |
| 2007/0060801 | A1 | 3/2007 | Neinast |
| 2007/0060814 | A1 | 3/2007 | Stafford |
| 2007/0060869 | A1 | 3/2007 | Tolle et al. |
| 2007/0060870 | A1 | 3/2007 | Tolle et al. |
| 2007/0060979 | A1 | 3/2007 | Strother et al. |
| 2007/0061167 | A1 | 3/2007 | Brown |
| 2007/0066873 | A1 | 3/2007 | Kamath et al. |
| 2007/0066956 | A1 | 3/2007 | Finkel |
| 2007/0068807 | A1 | 3/2007 | Feldman et al. |
| 2007/0073129 | A1 | 3/2007 | Shah et al. |

(56) References Cited

U.S. PATENT DOCUMENTS

| | | | |
|---|---|---|---|
| 2007/0078320 | A1 | 4/2007 | Stafford |
| 2007/0078321 | A1 | 4/2007 | Mazza et al. |
| 2007/0078322 | A1 | 4/2007 | Stafford |
| 2007/0078818 | A1 | 4/2007 | Zvitz et al. |
| 2007/0093786 | A1 | 4/2007 | Goldsmith et al. |
| 2007/0095661 | A1 | 5/2007 | Wang et al. |
| 2007/0106135 | A1 | 5/2007 | Sloan et al. |
| 2007/0108048 | A1 | 5/2007 | Wang et al. |
| 2007/0109117 | A1 | 5/2007 | Heitzmann et al. |
| 2007/0118030 | A1 | 5/2007 | Bruce et al. |
| 2007/0118588 | A1 | 5/2007 | Brown |
| 2007/0129621 | A1 | 6/2007 | Kellogg et al. |
| 2007/0142727 | A1 | 6/2007 | Zhang et al. |
| 2007/0149875 | A1 | 6/2007 | Ouyang et al. |
| 2007/0156033 | A1 | 7/2007 | Causey, III et al. |
| 2007/0156457 | A1 | 7/2007 | Brown |
| 2007/0163880 | A1 | 7/2007 | Woo et al. |
| 2007/0173706 | A1 | 7/2007 | Neinast et al. |
| 2007/0173709 | A1 | 7/2007 | Petisce et al. |
| 2007/0173710 | A1 | 7/2007 | Petisce et al. |
| 2007/0176867 | A1 | 8/2007 | Reggiardo et al. |
| 2007/0179434 | A1 | 8/2007 | Weinert et al. |
| 2007/0191701 | A1 | 8/2007 | Feldman et al. |
| 2007/0191702 | A1 | 8/2007 | Yodfat et al. |
| 2007/0199818 | A1 | 8/2007 | Petyt et al. |
| 2007/0202562 | A1 | 8/2007 | Curry et al. |
| 2007/0203407 | A1 | 8/2007 | Hoss et al. |
| 2007/0203539 | A1 | 8/2007 | Stone et al. |
| 2007/0203966 | A1 | 8/2007 | Brauker et al. |
| 2007/0207750 | A1 | 9/2007 | Brown et al. |
| 2007/0208244 | A1 | 9/2007 | Brauker et al. |
| 2007/0208246 | A1 | 9/2007 | Brauker et al. |
| 2007/0213605 | A1 | 9/2007 | Brown |
| 2007/0213657 | A1 | 9/2007 | Jennewine et al. |
| 2007/0219480 | A1 | 9/2007 | Kamen et al. |
| 2007/0227911 | A1 | 10/2007 | Wang et al. |
| 2007/0228071 | A1 | 10/2007 | Kamen et al. |
| 2007/0231846 | A1 | 10/2007 | Cosentino et al. |
| 2007/0232878 | A1 | 10/2007 | Kovatchev et al. |
| 2007/0232880 | A1 | 10/2007 | Siddiqui et al. |
| 2007/0233013 | A1 | 10/2007 | Schoenberg et al. |
| 2007/0235331 | A1 | 10/2007 | Simpson et al. |
| 2007/0244383 | A1 | 10/2007 | Talbot et al. |
| 2007/0249922 | A1 | 10/2007 | Peyser et al. |
| 2007/0251835 | A1 | 11/2007 | Mehta et al. |
| 2007/0253021 | A1 | 11/2007 | Mehta et al. |
| 2007/0255321 | A1 | 11/2007 | Gerber et al. |
| 2007/0255348 | A1 | 11/2007 | Holtzclaw |
| 2007/0255531 | A1 | 11/2007 | Drew |
| 2007/0258395 | A1 | 11/2007 | Jollota et al. |
| 2007/0270672 | A1 | 11/2007 | Hayter |
| 2007/0282299 | A1 | 12/2007 | Hellwig |
| 2007/0285238 | A1 | 12/2007 | Batra |
| 2007/0288265 | A1 | 12/2007 | Quinian et al. |
| 2007/0299617 | A1 | 12/2007 | Willis |
| 2008/0004515 | A1 | 1/2008 | Jennewine et al. |
| 2008/0004601 | A1 | 1/2008 | Jennewine et al. |
| 2008/0004904 | A1 | 1/2008 | Tran |
| 2008/0009692 | A1 | 1/2008 | Stafford |
| 2008/0009805 | A1 | 1/2008 | Ethelfeld |
| 2008/0012701 | A1 | 1/2008 | Kass et al. |
| 2008/0017522 | A1 | 1/2008 | Heller et al. |
| 2008/0018433 | A1 | 1/2008 | Pitt-Pladdy |
| 2008/0021666 | A1 | 1/2008 | Goode et al. |
| 2008/0021972 | A1 | 1/2008 | Huelskamp et al. |
| 2008/0029391 | A1 | 2/2008 | Mao et al. |
| 2008/0030369 | A1 | 2/2008 | Mann et al. |
| 2008/0033254 | A1 | 2/2008 | Kamath et al. |
| 2008/0039702 | A1 | 2/2008 | Hayter et al. |
| 2008/0045824 | A1 | 2/2008 | Tapsak et al. |
| 2008/0058773 | A1 | 3/2008 | John |
| 2008/0060955 | A1 | 3/2008 | Goodnow |
| 2008/0061961 | A1 | 3/2008 | John |
| 2008/0064943 | A1 | 3/2008 | Talbot et al. |
| 2008/0066305 | A1 | 3/2008 | Wang et al. |
| 2008/0071156 | A1 | 3/2008 | Brister et al. |
| 2008/0071328 | A1 | 3/2008 | Haubrich et al. |
| 2008/0081977 | A1 | 4/2008 | Hayter et al. |
| 2008/0083617 | A1 | 4/2008 | Simpson et al. |
| 2008/0086042 | A1 | 4/2008 | Brister et al. |
| 2008/0086044 | A1 | 4/2008 | Brister et al. |
| 2008/0086273 | A1 | 4/2008 | Shults et al. |
| 2008/0092638 | A1 | 4/2008 | Brenneman et al. |
| 2008/0097246 | A1 | 4/2008 | Stafford |
| 2008/0102441 | A1 | 5/2008 | Chen et al. |
| 2008/0103447 | A1 | 5/2008 | Reggiardo et al. |
| 2008/0108942 | A1 | 5/2008 | Brister et al. |
| 2008/0114228 | A1 | 5/2008 | McCluskey et al. |
| 2008/0114229 | A1 | 5/2008 | Brown |
| 2008/0119703 | A1 | 5/2008 | Brister et al. |
| 2008/0119705 | A1 | 5/2008 | Patel et al. |
| 2008/0119708 | A1 | 5/2008 | Budiman |
| 2008/0125636 | A1 | 5/2008 | Ward et al. |
| 2008/0127052 | A1 | 5/2008 | Rostoker |
| 2008/0139910 | A1 | 6/2008 | Mastrototaro et al. |
| 2008/0148873 | A1 | 6/2008 | Wang |
| 2008/0154099 | A1 | 6/2008 | Aspel et al. |
| 2008/0161666 | A1 | 7/2008 | Feldman et al. |
| 2008/0167572 | A1 | 7/2008 | Stivoric et al. |
| 2008/0169904 | A1 | 7/2008 | Schulman et al. |
| 2008/0172205 | A1 | 7/2008 | Breton et al. |
| 2008/0177149 | A1 | 7/2008 | Weinert et al. |
| 2008/0177165 | A1 | 7/2008 | Blomquist et al. |
| 2008/0183061 | A1 | 7/2008 | Goode, Jr. et al. |
| 2008/0183399 | A1 | 7/2008 | Goode, Jr. et al. |
| 2008/0188731 | A1 | 8/2008 | Brister et al. |
| 2008/0189051 | A1 | 8/2008 | Goode, Jr. et al. |
| 2008/0194934 | A1 | 8/2008 | Ray et al. |
| 2008/0194935 | A1 | 8/2008 | Brister et al. |
| 2008/0194936 | A1 | 8/2008 | Goode, Jr. et al. |
| 2008/0194937 | A1 | 8/2008 | Goode, Jr. et al. |
| 2008/0194938 | A1 | 8/2008 | Brister et al. |
| 2008/0195232 | A1 | 8/2008 | Carr-Brendel et al. |
| 2008/0195967 | A1 | 8/2008 | Goode, Jr. et al. |
| 2008/0197024 | A1 | 8/2008 | Simpson et al. |
| 2008/0200788 | A1 | 8/2008 | Brister et al. |
| 2008/0200789 | A1 | 8/2008 | Brister et al. |
| 2008/0200791 | A1 | 8/2008 | Simpson et al. |
| 2008/0201325 | A1 | 8/2008 | Doniger et al. |
| 2008/0208025 | A1 | 8/2008 | Shults et al. |
| 2008/0214900 | A1 | 9/2008 | Fennell et al. |
| 2008/0214910 | A1 | 9/2008 | Buck |
| 2008/0214915 | A1 | 9/2008 | Brister et al. |
| 2008/0214918 | A1 | 9/2008 | Brister et al. |
| 2008/0218180 | A1 | 9/2008 | Waffenschmidt et al. |
| 2008/0228051 | A1 | 9/2008 | Shults et al. |
| 2008/0228054 | A1 | 9/2008 | Shults et al. |
| 2008/0228055 | A1 | 9/2008 | Sher |
| 2008/0234943 | A1 | 9/2008 | Ray et al. |
| 2008/0235469 | A1 | 9/2008 | Drew |
| 2008/0242961 | A1 | 10/2008 | Brister et al. |
| 2008/0242963 | A1 | 10/2008 | Essenpreis et al. |
| 2008/0254544 | A1 | 10/2008 | Modzelewski et al. |
| 2008/0255438 | A1 | 10/2008 | Saidara et al. |
| 2008/0262469 | A1 | 10/2008 | Brister et al. |
| 2008/0267823 | A1 | 10/2008 | Wang et al. |
| 2008/0269571 | A1 | 10/2008 | Brown |
| 2008/0269687 | A1 | 10/2008 | Chong et al. |
| 2008/0269714 | A1 | 10/2008 | Mastrototaro et al. |
| 2008/0269723 | A1 | 10/2008 | Mastrototaro et al. |
| 2008/0275313 | A1 | 11/2008 | Brister et al. |
| 2008/0278332 | A1 | 11/2008 | Fennel et al. |
| 2008/0278333 | A1 | 11/2008 | Fennell et al. |
| 2008/0281179 | A1 | 11/2008 | Fennel et al. |
| 2008/0287761 | A1 | 11/2008 | Hayter |
| 2008/0287764 | A1 | 11/2008 | Rasdal et al. |
| 2008/0287765 | A1 | 11/2008 | Rasdal et al. |
| 2008/0287766 | A1 | 11/2008 | Rasdal et al. |
| 2008/0294024 | A1 | 11/2008 | Cosentino et al. |
| 2008/0296155 | A1 | 12/2008 | Shults et al. |
| 2008/0300476 | A1 | 12/2008 | Stafford |
| 2008/0300572 | A1 | 12/2008 | Rankers et al. |
| 2008/0306368 | A1 | 12/2008 | Goode, Jr. et al. |
| 2008/0306434 | A1 | 12/2008 | Dobbles et al. |

(56) References Cited

U.S. PATENT DOCUMENTS

| | | | |
|---|---|---|---|
| 2008/0306435 | A1 | 12/2008 | Kamath et al. |
| 2008/0306444 | A1 | 12/2008 | Brister et al. |
| 2008/0312512 | A1 | 12/2008 | Brukalo et al. |
| 2008/0312518 | A1 | 12/2008 | Jina et al. |
| 2008/0314395 | A1 | 12/2008 | Kovatchev et al. |
| 2008/0319085 | A1 | 12/2008 | Wright et al. |
| 2008/0319294 | A1 | 12/2008 | Taub et al. |
| 2008/0319295 | A1 | 12/2008 | Bernstein et al. |
| 2008/0319296 | A1 | 12/2008 | Bernstein et al. |
| 2008/0319414 | A1 | 12/2008 | Yodfat et al. |
| 2009/0005665 | A1 | 1/2009 | Hayter et al. |
| 2009/0005666 | A1 | 1/2009 | Shin et al. |
| 2009/0005729 | A1 | 1/2009 | Hendrixson et al. |
| 2009/0006034 | A1 | 1/2009 | Hayter et al. |
| 2009/0006061 | A1 | 1/2009 | Thukral et al. |
| 2009/0006133 | A1 | 1/2009 | Weinert et al. |
| 2009/0012376 | A1 | 1/2009 | Agus |
| 2009/0012377 | A1 | 1/2009 | Jennewine et al. |
| 2009/0012379 | A1 | 1/2009 | Goode, Jr. et al. |
| 2009/0018424 | A1 | 1/2009 | Kamath et al. |
| 2009/0018425 | A1 | 1/2009 | Ouyang et al. |
| 2009/0030293 | A1 | 1/2009 | Cooper et al. |
| 2009/0030294 | A1 | 1/2009 | Petisce et al. |
| 2009/0036747 | A1 | 2/2009 | Hayter et al. |
| 2009/0036758 | A1 | 2/2009 | Brauker et al. |
| 2009/0036763 | A1 | 2/2009 | Brauker et al. |
| 2009/0040022 | A1 | 2/2009 | Finkenzeller |
| 2009/0043181 | A1 | 2/2009 | Brauker et al. |
| 2009/0043182 | A1 | 2/2009 | Brauker et al. |
| 2009/0043525 | A1 | 2/2009 | Brauker et al. |
| 2009/0043541 | A1 | 2/2009 | Brauker et al. |
| 2009/0043542 | A1 | 2/2009 | Brauker et al. |
| 2009/0045055 | A1 | 2/2009 | Rhodes et al. |
| 2009/0048503 | A1 | 2/2009 | Dalal et al. |
| 2009/0054745 | A1 | 2/2009 | Jennewine et al. |
| 2009/0054747 | A1 | 2/2009 | Fennell |
| 2009/0054748 | A1 | 2/2009 | Feldman et al. |
| 2009/0054753 | A1 | 2/2009 | Robinson et al. |
| 2009/0062633 | A1 | 3/2009 | Brauker et al. |
| 2009/0062635 | A1 | 3/2009 | Brauker et al. |
| 2009/0063964 | A1 | 3/2009 | Huang et al. |
| 2009/0076356 | A1 | 3/2009 | Simpson et al. |
| 2009/0076360 | A1 | 3/2009 | Brister et al. |
| 2009/0076361 | A1 | 3/2009 | Kamath et al. |
| 2009/0082693 | A1 | 3/2009 | Stafford |
| 2009/0085768 | A1 | 4/2009 | Patel et al. |
| 2009/0085873 | A1 | 4/2009 | Betts et al. |
| 2009/0088614 | A1 | 4/2009 | Taub |
| 2009/0093687 | A1 | 4/2009 | Telfort et al. |
| 2009/0099427 | A1 | 4/2009 | Jina et al. |
| 2009/0099436 | A1 | 4/2009 | Brister et al. |
| 2009/0105554 | A1 | 4/2009 | Stahmann et al. |
| 2009/0105560 | A1 | 4/2009 | Solomon |
| 2009/0105568 | A1 | 4/2009 | Bugler |
| 2009/0105570 | A1 | 4/2009 | Sloan et al. |
| 2009/0105571 | A1 | 4/2009 | Fennell et al. |
| 2009/0112478 | A1 | 4/2009 | Mueller, Jr. et al. |
| 2009/0112626 | A1 | 4/2009 | Talbot et al. |
| 2009/0124877 | A1 | 5/2009 | Goode, Jr. et al. |
| 2009/0124878 | A1 | 5/2009 | Goode, Jr. et al. |
| 2009/0124879 | A1 | 5/2009 | Brister et al. |
| 2009/0124964 | A1 | 5/2009 | Leach et al. |
| 2009/0131768 | A1 | 5/2009 | Simpson et al. |
| 2009/0131769 | A1 | 5/2009 | Leach et al. |
| 2009/0131776 | A1 | 5/2009 | Simpson et al. |
| 2009/0131777 | A1 | 5/2009 | Simpson et al. |
| 2009/0131860 | A1 | 5/2009 | Nielsen |
| 2009/0137886 | A1 | 5/2009 | Shariati et al. |
| 2009/0137887 | A1 | 5/2009 | Shariati et al. |
| 2009/0143659 | A1 | 6/2009 | Li et al. |
| 2009/0143660 | A1 | 6/2009 | Brister et al. |
| 2009/0143661 | A1 | 6/2009 | Taub et al. |
| 2009/0143725 | A1 | 6/2009 | Peyser et al. |
| 2009/0149728 | A1 | 6/2009 | Van Antwerp et al. |
| 2009/0150186 | A1 | 6/2009 | Cohen et al. |
| 2009/0156919 | A1 | 6/2009 | Brister et al. |
| 2009/0156924 | A1 | 6/2009 | Shariati et al. |
| 2009/0163790 | A1 | 6/2009 | Brister et al. |
| 2009/0163791 | A1 | 6/2009 | Brister et al. |
| 2009/0163855 | A1 | 6/2009 | Shin et al. |
| 2009/0177068 | A1 | 7/2009 | Stivoric et al. |
| 2009/0178459 | A1 | 7/2009 | Li et al. |
| 2009/0182217 | A1 | 7/2009 | Li et al. |
| 2009/0182517 | A1 | 7/2009 | Gandhi et al. |
| 2009/0189738 | A1 | 7/2009 | Hermle |
| 2009/0192366 | A1 | 7/2009 | Mensinger et al. |
| 2009/0192380 | A1 | 7/2009 | Shariati et al. |
| 2009/0192722 | A1 | 7/2009 | Shariati et al. |
| 2009/0192724 | A1 | 7/2009 | Brauker et al. |
| 2009/0192745 | A1 | 7/2009 | Kamath et al. |
| 2009/0192751 | A1 | 7/2009 | Kamath et al. |
| 2009/0203981 | A1 | 8/2009 | Brauker et al. |
| 2009/0204341 | A1 | 8/2009 | Brauker et al. |
| 2009/0216100 | A1 | 8/2009 | Ebner et al. |
| 2009/0216103 | A1 | 8/2009 | Brister et al. |
| 2009/0234200 | A1 | 9/2009 | Husheer |
| 2009/0237216 | A1 | 9/2009 | Twitchell, Jr. |
| 2009/0240120 | A1 | 9/2009 | Mensinger et al. |
| 2009/0240128 | A1 | 9/2009 | Mensinger et al. |
| 2009/0240193 | A1 | 9/2009 | Mensinger et al. |
| 2009/0242399 | A1 | 10/2009 | Kamath et al. |
| 2009/0242425 | A1 | 10/2009 | Kamath et al. |
| 2009/0247855 | A1 | 10/2009 | Boock et al. |
| 2009/0247856 | A1 | 10/2009 | Boock et al. |
| 2009/0248380 | A1 | 10/2009 | Brown |
| 2009/0253973 | A1 | 10/2009 | Bashan et al. |
| 2009/0267765 | A1 | 10/2009 | Greene et al. |
| 2009/0287073 | A1 | 11/2009 | Boock et al. |
| 2009/0287074 | A1 | 11/2009 | Shults et al. |
| 2009/0289796 | A1 | 11/2009 | Blumberg |
| 2009/0294277 | A1 | 12/2009 | Thomas et al. |
| 2009/0298182 | A1 | 12/2009 | Schulat et al. |
| 2009/0299155 | A1 | 12/2009 | Yang et al. |
| 2009/0299156 | A1 | 12/2009 | Simpson et al. |
| 2009/0299162 | A1 | 12/2009 | Brauker et al. |
| 2009/0299276 | A1 | 12/2009 | Brauker et al. |
| 2010/0004522 | A1 | 1/2010 | Varela |
| 2010/0010324 | A1 | 1/2010 | Brauker et al. |
| 2010/0010331 | A1 | 1/2010 | Brauker et al. |
| 2010/0010332 | A1 | 1/2010 | Brauker et al. |
| 2010/0014626 | A1 | 1/2010 | Fennell et al. |
| 2010/0016687 | A1 | 1/2010 | Brauker et al. |
| 2010/0016698 | A1 | 1/2010 | Rasdal et al. |
| 2010/0022855 | A1 | 1/2010 | Brauker et al. |
| 2010/0022988 | A1 | 1/2010 | Wochner et al. |
| 2010/0030038 | A1 | 2/2010 | Brauker et al. |
| 2010/0030053 | A1 | 2/2010 | Goode, Jr. et al. |
| 2010/0030484 | A1 | 2/2010 | Brauker et al. |
| 2010/0030485 | A1 | 2/2010 | Brauker et al. |
| 2010/0036215 | A1 | 2/2010 | Goode, Jr. et al. |
| 2010/0036216 | A1 | 2/2010 | Goode, Jr. et al. |
| 2010/0036222 | A1 | 2/2010 | Goode, Jr. et al. |
| 2010/0036223 | A1 | 2/2010 | Goode, Jr. et al. |
| 2010/0036225 | A1 | 2/2010 | Goode, Jr. et al. |
| 2010/0041971 | A1 | 2/2010 | Goode, Jr. et al. |
| 2010/0045425 | A1 | 2/2010 | Chivallier |
| 2010/0045465 | A1 | 2/2010 | Brauker et al. |
| 2010/0049024 | A1 | 2/2010 | Saint et al. |
| 2010/0052899 | A1 | 3/2010 | Bruce |
| 2010/0057041 | A1 | 3/2010 | Hayter et al. |
| 2010/0063373 | A1 | 3/2010 | Kamath et al. |
| 2010/0064764 | A1 | 3/2010 | Hayter et al. |
| 2010/0076283 | A1 | 3/2010 | Simpson et al. |
| 2010/0076284 | A1 | 3/2010 | Bernstein et al. |
| 2010/0081905 | A1 | 4/2010 | Bommakanti et al. |
| 2010/0081908 | A1 | 4/2010 | Dobbles et al. |
| 2010/0081909 | A1 | 4/2010 | Budiman et al. |
| 2010/0081910 | A1 | 4/2010 | Brister et al. |
| 2010/0081953 | A1 | 4/2010 | Syeda-Mahmood et al. |
| 2010/0087724 | A1 | 4/2010 | Brauker et al. |
| 2010/0093786 | A1 | 4/2010 | Watanabe et al. |
| 2010/0094111 | A1 | 4/2010 | Heller et al. |
| 2010/0094251 | A1 | 4/2010 | Estes et al. |
| 2010/0096259 | A1 | 4/2010 | Zhang et al. |

(56) References Cited

U.S. PATENT DOCUMENTS

2010/0099970 A1 4/2010 Shults et al.
2010/0099971 A1 4/2010 Shults et al.
2010/0105999 A1 4/2010 Dixon et al.
2010/0111066 A1 5/2010 Mehta
2010/0119693 A1 5/2010 Tapsak et al.
2010/0121167 A1 5/2010 McGarraugh et al.
2010/0121169 A1 5/2010 Petisce et al.
2010/0141429 A1 6/2010 Bruegger et al.
2010/0141656 A1 6/2010 Krieftewirth
2010/0145172 A1 6/2010 Petisce et al.
2010/0146300 A1 6/2010 Brown
2010/0152554 A1 6/2010 Steine et al.
2010/0160759 A1 6/2010 Celentano et al.
2010/0160760 A1 6/2010 Shults et al.
2010/0161269 A1 6/2010 Kamath et al.
2010/0168538 A1 7/2010 Keenan et al.
2010/0168540 A1 7/2010 Kamath et al.
2010/0168541 A1 7/2010 Kamath et al.
2010/0168542 A1 7/2010 Kamath et al.
2010/0168543 A1 7/2010 Kamath et al.
2010/0168544 A1 7/2010 Kamath et al.
2010/0168545 A1 7/2010 Kamath et al.
2010/0168546 A1 7/2010 Kamath et al.
2010/0168657 A1 7/2010 Kamath et al.
2010/0174157 A1 7/2010 Brister et al.
2010/0174158 A1 7/2010 Kamath et al.
2010/0174163 A1 7/2010 Brister et al.
2010/0174164 A1 7/2010 Brister et al.
2010/0174165 A1 7/2010 Brister et al.
2010/0174166 A1 7/2010 Brister et al.
2010/0174167 A1 7/2010 Kamath et al.
2010/0174168 A1 7/2010 Goode et al.
2010/0174266 A1 7/2010 Estes
2010/0179399 A1 7/2010 Goode et al.
2010/0179400 A1 7/2010 Brauker et al.
2010/0179401 A1 7/2010 Rasdal et al.
2010/0179402 A1 7/2010 Goode et al.
2010/0179404 A1 7/2010 Kamath et al.
2010/0179405 A1 7/2010 Goode et al.
2010/0179407 A1 7/2010 Goode et al.
2010/0179408 A1 7/2010 Kamath et al.
2010/0179409 A1 7/2010 Kamath et al.
2010/0185065 A1 7/2010 Goode et al.
2010/0185069 A1 7/2010 Brister et al.
2010/0185070 A1 7/2010 Brister et al.
2010/0185071 A1 7/2010 Simpson et al.
2010/0185072 A1 7/2010 Goode et al.
2010/0185073 A1 7/2010 Goode et al.
2010/0185074 A1 7/2010 Goode et al.
2010/0185075 A1 7/2010 Brister et al.
2010/0185175 A1 7/2010 Kamen et al.
2010/0190435 A1 7/2010 Cook et al.
2010/0191082 A1 7/2010 Brister et al.
2010/0191085 A1 7/2010 Budiman
2010/0198034 A1 8/2010 Thomas et al.
2010/0198035 A1 8/2010 Kamath et al.
2010/0198036 A1 8/2010 Kamath et al.
2010/0198142 A1 8/2010 Sloan et al.
2010/0213057 A1 8/2010 Feldman et al.
2010/0213080 A1 8/2010 Celentano et al.
2010/0230285 A1 9/2010 Hoss et al.
2010/0234710 A1 9/2010 Budiman et al.
2010/0257490 A1 10/2010 Lyon et al.
2010/0261987 A1 10/2010 Kamath et al.
2010/0268157 A1 10/2010 Wehba et al.
2010/0274111 A1 10/2010 Say et al.
2010/0274218 A1 10/2010 Yodfat et al.
2010/0280441 A1 11/2010 Willinska et al.
2010/0280782 A1 11/2010 Harper
2010/0298686 A1 11/2010 Reggiardo et al.
2010/0302979 A1 12/2010 Jukka
2010/0312176 A1 12/2010 Lauer et al.
2010/0313105 A1 12/2010 Nekoomaram et al.
2010/0317952 A1 12/2010 Budiman et al.
2010/0324392 A1 12/2010 Yee et al.
2010/0326842 A1 12/2010 Mazza et al.
2010/0327063 A1 12/2010 Medina et al.
2011/0003610 A1 1/2011 Key et al.
2011/0004085 A1 1/2011 Mensinger et al.
2011/0004276 A1 1/2011 Blair et al.
2011/0009727 A1 1/2011 Mensinger et al.
2011/0009813 A1 1/2011 Rankers
2011/0024043 A1 2/2011 Boock et al.
2011/0024307 A1 2/2011 Simpson et al.
2011/0027127 A1 2/2011 Simpson et al.
2011/0027453 A1 2/2011 Boock et al.
2011/0027458 A1 2/2011 Boock et al.
2011/0028815 A1 2/2011 Simpson et al.
2011/0028816 A1 2/2011 Simpson et al.
2011/0029247 A1 2/2011 Kalathil
2011/0031986 A1 2/2011 Bhat et al.
2011/0040163 A1 2/2011 Telson et al.
2011/0044333 A1 2/2011 Sicurello et al.
2011/0077490 A1 3/2011 Simpson et al.
2011/0082484 A1 4/2011 Saravia et al.
2011/0105955 A1 5/2011 Yudovsky et al.
2011/0106126 A1 5/2011 Love et al.
2011/0112696 A1 5/2011 Yodfat et al.
2011/0125000 A1 5/2011 Rantala
2011/0148905 A1 6/2011 Simmons et al.
2011/0152637 A1 6/2011 Kateraas et al.
2011/0173308 A1 7/2011 Gutekunst
2011/0177780 A1 7/2011 Sato et al.
2011/0178717 A1 7/2011 Goodnow et al.
2011/0190603 A1 8/2011 Stafford
2011/0191044 A1 8/2011 Stafford
2011/0193704 A1 8/2011 Harper et al.
2011/0201911 A1 8/2011 Johnson et al.
2011/0202495 A1 8/2011 Gawlick
2011/0208027 A1 8/2011 Wagner et al.
2011/0208155 A1 8/2011 Palerm et al.
2011/0213225 A1 9/2011 Bernstein et al.
2011/0257495 A1 10/2011 Hoss et al.
2011/0257895 A1 10/2011 Brauker et al.
2011/0263958 A1 10/2011 Brauker et al.
2011/0282327 A1 11/2011 Kellogg et al.
2011/0282671 A1 11/2011 Dicks et al.
2011/0287528 A1 11/2011 Fern et al.
2011/0288574 A1 11/2011 Curry et al.
2011/0289497 A1 11/2011 Kiaie et al.
2011/0320130 A1 12/2011 Valdes et al.
2012/0003933 A1 1/2012 Baker et al.
2012/0035448 A1 2/2012 Taub et al.
2012/0078071 A1 3/2012 Bohm et al.
2012/0108931 A1 5/2012 Taub et al.
2012/0108934 A1 5/2012 Valdes et al.
2012/0123227 A1 5/2012 Sun et al.
2012/0165626 A1 6/2012 Irina et al.
2012/0165640 A1 6/2012 Galley et al.
2012/0173200 A1 7/2012 Breton et al.
2012/0179017 A1 7/2012 Satou et al.
2012/0182917 A1 7/2012 Edlund
2012/0200410 A1 8/2012 Taub et al.
2012/0209099 A1 8/2012 Ljuhs et al.
2012/0215462 A1 8/2012 Goode et al.
2012/0237022 A1 9/2012 Berson et al.
2012/0255875 A1 10/2012 Vicente et al.
2012/0260323 A1 10/2012 San et al.
2012/0265035 A1 10/2012 Bohm et al.
2012/0313785 A1 12/2012 Hanson et al.
2013/0035575 A1 2/2013 Mayou et al.
2013/0078912 A1 3/2013 San et al.
2013/0113632 A1 5/2013 Bernstein et al.
2013/0225959 A1 8/2013 Bugler
2013/0231541 A1 9/2013 Hayter et al.
2013/0235166 A1 9/2013 Jones et al.
2013/0310896 A1 11/2013 Mass
2014/0088382 A1 3/2014 Bernstein et al.
2014/0221966 A1 8/2014 Buckingham et al.
2014/0266776 A1 9/2014 Miller et al.
2014/0266785 A1 9/2014 Miller et al.
2014/0273821 A1 9/2014 Miller et al.
2014/0273858 A1 9/2014 Panther et al.
2014/0275898 A1 9/2014 Taub et al.

(56) References Cited

U.S. PATENT DOCUMENTS

| | | | | |
|---|---|---|---|---|
| 2014/0313052 | A1 | 10/2014 | Yarger et al. | |
| 2014/0379273 | A1 | 12/2014 | Petisce et al. | |
| 2015/0038818 | A1 | 2/2015 | Cole | |
| 2015/0089222 | A1 | 3/2015 | White et al. | |
| 2015/0118658 | A1 | 4/2015 | Mayou et al. | |
| 2015/0123810 | A1 | 5/2015 | Hernandez-Rosas et al. | |
| 2015/0164391 | A1 | 6/2015 | Hernandez-Rosas et al. | |
| 2015/0164392 | A1 | 6/2015 | Taub et al. | |
| 2015/0205947 | A1 | 7/2015 | Berman et al. | |
| 2015/0207796 | A1 | 7/2015 | Love et al. | |
| 2015/0241407 | A1 | 8/2015 | Ou et al. | |
| 2015/0289124 | A1 | 10/2015 | Palin et al. | |
| 2015/0351674 | A1 | 12/2015 | Thomas et al. | |
| 2016/0066826 | A1 | 3/2016 | Larvenz et al. | |
| 2016/0073879 | A1 | 3/2016 | Mensinger et al. | |
| 2016/0081597 | A1 | 3/2016 | Bhavaraju et al. | |
| 2016/0165649 | A1 | 6/2016 | Polo et al. | |
| 2016/0210099 | A1 | 7/2016 | Hampapuram et al. | |
| 2016/0234020 | A1 | 8/2016 | Nix | |
| 2016/0345376 | A1 | 11/2016 | Yang et al. | |
| 2017/0201811 | A1 | 7/2017 | Tateda | |
| 2018/0192927 | A1 | 7/2018 | Taub et al. | |
| 2018/0325434 | A1 | 11/2018 | Bernstein et al. | |
| 2019/0364111 | A1 | 11/2019 | Sloan et al. | |
| 2020/0008721 | A1 | 1/2020 | Wedekind et al. | |
| 2021/0000396 | A1 | 1/2021 | Bernstein et al. | |
| 2021/0151182 | A1 | 5/2021 | Bernstein et al. | |
| 2021/0169384 | A1 | 6/2021 | Taub et al. | |
| 2022/0068473 | A1 | 3/2022 | Miller et al. | |
| 2022/0071526 | A1 | 3/2022 | Taub et al. | |
| 2022/0095968 | A1 | 3/2022 | Wang et al. | |
| 2023/0210413 | A1 | 7/2023 | Taub et al. | |
| 2024/0298933 | A1 | 9/2024 | Taub et al. | |
| 2024/0423515 | A1* | 12/2024 | Taub ...................... | G16H 40/67 |

FOREIGN PATENT DOCUMENTS

| | | | |
|---|---|---|---|
| EP | 0098592 | | 1/1984 |
| EP | 0127958 | | 12/1984 |
| EP | 0320109 | | 6/1989 |
| EP | 0353328 | | 2/1990 |
| EP | 0390390 | | 10/1990 |
| EP | 0396788 | | 11/1990 |
| EP | 0286118 | | 1/1995 |
| EP | 1048264 | | 11/2000 |
| JP | 4469504 | B2 | 5/2010 |
| WO | WO 1996/025089 | | 8/1996 |
| WO | WO 1996/035370 | | 11/1996 |
| WO | WO 1998/035053 | | 8/1998 |
| WO | 99/58190 | A1 | 11/1999 |
| WO | WO 1999/056613 | | 11/1999 |
| WO | WO 2000/049940 | | 8/2000 |
| WO | WO 2000/059370 | | 10/2000 |
| WO | WO 2000/074753 | | 12/2000 |
| WO | WO 2000/078992 | | 12/2000 |
| WO | WO 2001/052935 | | 7/2001 |
| WO | WO 2001/054753 | | 8/2001 |
| WO | 02/15778 | A1 | 2/2002 |
| WO | WO 2002/016905 | | 2/2002 |
| WO | 02/58537 | A2 | 8/2002 |
| WO | 02/71305 | A2 | 9/2002 |
| WO | 03/26728 | A1 | 3/2003 |
| WO | 03/76893 | A2 | 9/2003 |
| WO | 03/85372 | A2 | 10/2003 |
| WO | WO 2003/082091 | | 10/2003 |
| WO | 2004/006982 | A2 | 1/2004 |
| WO | 2004/061420 | A2 | 7/2004 |
| WO | 2005/018450 | A2 | 3/2005 |
| WO | 2005/041766 | A1 | 5/2005 |
| WO | 2005/046780 | A1 | 5/2005 |
| WO | 2005/089103 | A2 | 9/2005 |
| WO | 2005/119524 | A2 | 12/2005 |
| WO | WO 2006/024671 | | 3/2006 |
| WO | 2006/040083 | A1 | 4/2006 |
| WO | 2006/079114 | A2 | 7/2006 |
| WO | 2006/086423 | A2 | 8/2006 |
| WO | 2006/094513 | A2 | 9/2006 |
| WO | 2006/118947 | A2 | 11/2006 |
| WO | 2006/121921 | A2 | 11/2006 |
| WO | 2007/002189 | A2 | 1/2007 |
| WO | 2007/016399 | A2 | 2/2007 |
| WO | 2007/027788 | A2 | 3/2007 |
| WO | 2007/041069 | A2 | 4/2007 |
| WO | 2007/041070 | A2 | 4/2007 |
| WO | 2007/041248 | A2 | 4/2007 |
| WO | 2007/053832 | A2 | 5/2007 |
| WO | 2007/056638 | A2 | 5/2007 |
| WO | 2007/097754 | A1 | 8/2007 |
| WO | 2007/101223 | A2 | 9/2007 |
| WO | 2007/104755 | A1 | 9/2007 |
| WO | 2007/120363 | A2 | 10/2007 |
| WO | 2007/126444 | A2 | 11/2007 |
| WO | 2007/143225 | A2 | 12/2007 |
| WO | WO 2008/001366 | | 1/2008 |
| WO | 2008/065646 | A1 | 6/2008 |
| WO | 2008/073813 | A1 | 6/2008 |
| WO | WO 2008/086541 | | 7/2008 |
| WO | 2008/114223 | A1 | 9/2008 |
| WO | 2008/115409 | A1 | 9/2008 |
| WO | 2008/144325 | A1 | 11/2008 |
| WO | 2008/157821 | A1 | 12/2008 |
| WO | 2009/007287 | A1 | 1/2009 |
| WO | 2009/035773 | A1 | 3/2009 |
| WO | 2009/039013 | A1 | 3/2009 |
| WO | 2009/051832 | A1 | 4/2009 |
| WO | 2009/105709 | A1 | 8/2009 |
| WO | WO 2010/077329 | | 7/2010 |
| WO | 2012/154286 | A1 | 11/2012 |
| WO | 2013/044153 | A1 | 3/2013 |
| WO | 2013/069894 | A1 | 5/2013 |
| WO | 2013/090731 | A1 | 6/2013 |
| WO | 2013/090791 | A1 | 6/2013 |
| WO | 2014/011488 | A2 | 1/2014 |
| WO | 2014/105631 | A2 | 7/2014 |
| WO | 2014/158405 | A2 | 10/2014 |
| WO | 2014/165172 | A1 | 10/2014 |
| WO | 2014/179343 | A1 | 11/2014 |
| WO | WO 2015/046823 | A1 | 4/2015 |
| WO | 2015/069797 | A1 | 5/2015 |
| WO | 2015/194381 | A1 | 12/2015 |
| WO | 2016/064184 | A1 | 4/2016 |
| WO | 2016/092448 | A1 | 6/2016 |
| WO | 2016/101774 | A1 | 6/2016 |
| WO | 2017/172781 | A1 | 10/2017 |
| WO | 2018/017484 | A1 | 1/2018 |
| WO | 2018/075333 | A2 | 4/2018 |
| WO | WO 2020/242964 | A1 | 12/2020 |

OTHER PUBLICATIONS

U.S. Appl. No. 15/916,255, Nov. 5, 2020 Issue Fee Payment.
U.S. Appl. No. 15/916,255, Aug. 5, 2020 Notice of Allowance.
Armour, J. C., et al., "Application of Chronic Intravascular Blood Glucose Sensor in Dogs", Diabetes, vol. 39, 1990, pp. 1519-1526.
Aussedat, B., et al., "A User-Friendly Method for Calibrating a Subcutaneous Glucose Sensor-Based Hypoglycemic Alarm", Biosensors & Bioelectronics, vol. 12, No. 11, 1997, pp. 1061-1070.
Bennion, N., et al., "Alternate Site Glucose Testing: A Crossover Design", Diabetes Technology & Therapeutics, vol. 4, No. 1, 2002, pp. 25-33.
Blank, T. B., et al., "Clinical Results from a Non-Invasive Blood Glucose Monitor", Optical Diagnostics and Sensing of Biological Fluids and Glucose and Cholesterol Monitoring II, Proceedings of SPIE, vol. 4624, 2002, pp. 1-10.
Brooks, S. L., et al., "Development of an On-Line Glucose Sensor for Fermentation Monitoring", Biosensors, vol. 3, 1987/88, pp. 45-56.
Cass, A. E., et al., "Ferrocene-Medicated Enzyme Electrode for Amperometric Determination of Glucose", Analytical Chemistry, vol. 56, No. 4, 1984, 667-671.
Cheyne, E. H., et al., "Performance of a Continuous Glucose Monitoring System During Controlled Hypoglycaemia in Healthy

(56) References Cited

OTHER PUBLICATIONS

Volunteers", Diabetes Technology & Therapeutics, vol. 4, No. 5, 2002, pp. 607-613.
Csoregi, E., et al., "Design and Optimization of a Selective Subcutaneously Implantable Glucose Electrode Based on 'Wired' Glucose Oxidase", Analytical Chemistry, vol. 67, No. 7, 1995, pp. 1240-1244.
U.S. Appl. No. 15/916,255, Jul. 23, 2020 Response to Non-Final Office Action.
U.S. Appl. No. 15/916,255, Apr. 23, 2020 Non-Final Office Action.
Feldman, B., et al., "A Continuous Glucose Sensor Based on Wired EnzymeTM Technology—Results from a 3-Day Trial in Patients with Type 1 Diabetes", Diabetes Technology & Therapeutics, vol. 5, No. 5, 2003, pp. 769-779.
Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.
Garg, S., et al., "Improvement in Glycemic Excursions with a Transcutaneous, Real-Time Continuous Glucose Sensor", Diabetes Care, vol. 29, No. 1, 2006, pp. 44-50.
Isermann, R., "Supervision, Fault-Detection and Fault-Diagnosis Methods—An Introduction", Control Engineering Practice, vol. 5, No. 5, 1997, pp. 639-652.
Isermann, R., et al., "Trends in the Application of Model-Based Fault Detection and Diagnosis of Technical Processes", Control Engineering Practice, vol. 5, No. 5, 1997, pp. 709-719.
Johnson, P. C., "Peripheral Circulation", John Wiley & Sons, 1978, pp. 198.
Jovanovic, L., "The Role of Continuous Glucose Monitoring in Gestational Diabetes Mellitus", Diabetes Technology & Therapeutics, vol. 2, Sup. 1, 2000, pp. S67-S71.
Jungheim, K., et al., "How Rapid Does Glucose Concentration Change in Daily Life of Patients with Type 1 Diabetes?", 2002, pp. 250.
Jungheim, K., et al., "Risky Delay of Hypoglycemia Detection by Glucose Monitoring at the Arm", Diabetes Care, vol. 24, No. 7, 2001, pp. 1303-1304.
Kaplan, S. M., "Wiley Electrical and Electronics Engineering Dictionary", IEEE Press, 2004, pp. 141, 142, 548, 549.
Li, Y., et al., "In Vivo Release From a Drug Delivery MEMS Device", Journal of Controlled Release, vol. 100, 2004, 99. 211-219.
Lodwig, V., et al., "Continuous Glucose Monitoring with Glucose Sensors: Calibration and Assessment Criteria", Diabetes Technology & Therapeutics, vol. 5, No. 4, 2003, pp. 573-587.
Lortz, J., et al., "What is Bluetooth? We Explain The Newest Short-Range Connectivity Technology", Smart Computing Learning Series, Wireless Computing, vol. 8, Issue 5, 2002, pp. 72-74.
Malin, S. F., et al., "Noninvasive Prediction of Glucose by Near-Infrared Diffuse Reflectance Spectoscopy", Clinical Chemistry, vol. 45, No. 9, 1999, pp. 1651-1658.
McGarraugh, G., et al., "Glucose Measurements Using Blood Extracted from the Forearm and the Finger", TheraSense, Inc., 2001, 16 Pages.
McGarraugh, G., et al., "Physiological Influences on Off-Finger Glucose Testing", Diabetes Technology & Therapeutics, vol. 3, No. 3, 2001, pp. 367-376.
McKean, B. D., et al., "A Telemetry-Instrumentation System for Chronically Implanted Glucose and Oxygen Sensors", IEEE Transactions on Biomedical Engineering, vol. 35, No. 7, 1988, pp. 526-532.
Morbiducci, U, et al., "Improved Usability of the Minimal Model of Insulin Sensitivity Based on an Automated Approach and Genetic Algorithms for Parameter Estimation", Clinical Science, vol. 112, 2007, pp. 257-263.
Mougiakakou, et al., "A Real Time Simulation Model of Glucose-Insulin Metabolism for Type 1 Diabetes Patients", Proceedings of the 2005 IEEE, 2005, pp. 298-301.
Panteleon, A. E., et al., "The Role of the Independent Variable to Glucose Sensor Calibration", Diabetes Technology & Therapeutics, vol. 5, No. 3, 2003, pp. 401-410.
Parker, R., et al., "Robust H∞ Glucose Control in Diabetes Using a Physiological Model", AIChE Journal, vol. 46, No. 12, 2000, pp. 2537-2549.
Pickup, J., et al., "Implantable Glucose Sensors: Choosing the Appropriate Sensing Strategy", Biosensors, vol. 3, 1987/88, pp. 335-346.
Pickup, J., et al., "In Vivo Molecular Sensing in Diabetes Mellitus: An Implantable Glucose Sensor with Direct Electron Transfer", Diabetologia, vol. 32, 1989, pp. 213-217.
Pishko, M. V., et al., "Amperometric Glucose Microelectrodes Prepared Through Immobilization of Glucose Oxidase in Redox Hydrogels", Analytical Chemistry, vol. 63, No. 20, 1991, pp. 2268-2272.
Quinn, C. P., et al., "Kinetics of Glucose Delivery to Subcutaneous Tissue in Rats Measured with 0.3-mm Amperometric Microsensors", The American Physiological Society, 1995, E155-E161.
Roe, J. N., et al., "Bloodless Glucose Measurements", Critical Review in Therapeutic Drug Carrier Systems, vol. 15, Issue 3, 1998, pp. 199-241.
Sakakida, M., et al., "Development of Ferrocene-Mediated Needle-Type Glucose Sensor as a Measure of True Subcutaneous Tissue Glucose Concentrations", Artificial Organs Today, vol. 2, No. 2, 1992, pp. 145-158.
Sakakida, M., et al., "Ferrocene-Mediated Needle-Type Glucose Sensor Covered with Newly Designed Biocompatible Membrane", Sensors and Actuators B, vol. 13-14, 1993, pp. 319-322.
Salehi, C., et al., "A Telemetry-Instrumentation System for Long-Term Implantable Glucose and Oxygen Sensors", Analytical Letters, vol. 29, No. 13, 1996, pp. 2289-2308.
Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294-299.
Shaw, G. W., et al., "In Vitro Testing of a Simply Constructed, Highly Stable Glucose Sensor Suitable for Implantation in Diabetic Patients", Biosensors & Bioelectronics, vol. 6, 1991, pp. 401-406.
Shichiri, M., et al., "Glycaemic Control in Pancreatectomized Dogs with a Wearable Artificial Endocrine Pancreas", Diabetologia, vol. 24, 1983, pp. 179-184.
Shichiri, M., et al., "In Vivo Characteristics of Needle-Type Glucose Sensor—Measurements of Subcutaneous Glucose Concentrations in Human Volunteers", Hormone and Metabolic Research Supplement Series, vol. 20, 1988, pp. 17-20.
Shichiri, M., et al., "Membrane Design for Extending the Long-Life of an Implantable Glucose Sensor", Diabetes Nutrition and Metabolism, vol. 2, 1989, pp. 309-313.
Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.
Shichiri, M., et al., "Telemetry Glucose Monitoring Device with Needle-Type Glucose Sensor: A Useful Tool for Blood Glucose Monitoring in Diabetic Individuals", Diabetes Care, vol. 9, No. 3, 1986, pp. 298-301.
Shichiri, M., et al., "Wearable Artificial Endocrine Pancreas with Needle-Type Glucose Sensor", The Lancet, 1982, pp. 1129-1131.
Shults, M. C., et al., "A Telemetry-Instrumentation System for Monitoring Multiple Subcutaneously Implanted Glucose Sensors", IEEE Transactions on Biomedical Engineering, vol. 41, No. 10, 1994, pp. 937-942.
Sternberg, R., et al., "Study and Development of Multilayer Needle-Type Enzyme-Based Glucose Microsensors", Biosensors, vol. 4, 1988, pp. 27-40.
Thompson, M., et al., "In Vivo Probes: Problems and Perspectives", Clinical Biochemistry, vol. 19, 1986, pp. 255-261.
Turner, A., et al., "Diabetes Mellitus: Biosensors for Research and Management", Biosensors, vol. 1, 1985, pp. 85-115.
Updike, S. J., et al., "Principles of Long-Term Fully Implanted Sensors with Emphasis on Radiotelemetric Monitoring of Blood

(56) References Cited

OTHER PUBLICATIONS

Glucose from Inside a Subcutaneous Foreign Body Capsule (FBC)", Biosensors in the Body: Continuous in Vivo Monitoring, Chapter 4, 1997, pp. 117-137.
Velho, G., et al., "Strategies for Calibrating a Subcutaneous Glucose Sensor", Biomedica Biochimica Acta, vol. 48, 1989, pp. 957-964.
Wilson, G. S., et al., "Progress Toward the Development of an Implantable Sensor for Glucose", Clinical Chemistry, vol. 38, No. 9, 1992, pp. 1613-1617.
U.S. Appl. No. 12/147,464, Notice of Allowance mailed Jan. 24, 2012.
U.S. Appl. No. 12/147,464, Office Action mailed Oct. 23, 2014.
U.S. Appl. No. 14/629,447, Office Action mailed Aug. 10, 2017.
U.S. Appl. No. 14/629,447, Notice of Allowance mailed Dec. 5, 2017.
U.S. Appl. No. 18/183,773, Sep. 8, 2023 Non-Final Office Action.
U.S. Appl. No. 18/830,212, Dec. 6, 2024 Non-Final Office Action.
Notice of Allowance received for U.S. Appl. No. 17/531,271, mailed on Oct. 13, 2022.
Notice of Allowance received for U.S. Appl. No. 18/183,773, mailed on Apr. 15, 2024.
Notice of Allowance received for U.S. Appl. No. 18/183,773, mailed on Mar. 20, 2024.
Notice of Allowance received for U.S. Appl. No. 18/183,773, mailed on Sep. 26, 2025, 9 pages.
Omre, "Bluetooth Low Energy: Wireless Connectivity for Medical Monitoring," Journal of Diabetes Science and Technology, vol. 4, Issue 2, 457-463, Mar. 2010.
Padgette et al., "Guide to Bluetooth Security. Recommendations of the National Institute of Standards and Technology," NIST Special Publication 800-121, Revision 1, Jun. 2012, 47 pgs.
Padgette, John, et al., Recommendations of the National Institute of Standards and Technology, Guide to Bluetooth Security Jun. 2012.
Paradigm@ REAL-Time Revel™ Insulin Pump User Guide, Medtronic Minimed, 2009, 179 pages.
Pete Sorrells, "Passive RFID Basics", Microchip Technology Inc, DS00680B, pp. 1-5 (1998).
Place et al., "DiAs Web Monitoring: A Real-Time Remote Monitoring System Designed for Artificial Pancreas Outpatient Trials," Journal of Diabetes Science and Technology vol. 7, Issue 6, 1427-1435 (2013).
Press Coverage ofFreeStyle Libre launch, Antonia Giese, retrieved from https://www.bild. de/ratgeber/gesundheit/diabetes/hightech-zucker-sensor-diabetes-test-freestyle-libre-flash-37732134.bild. html, 8 pages Sep. 20, 2014 (with an English Abstract).
Press Release, Medtronic, "Medtronic Launches First-of-Its Kind mySentry™ Remote Glucose Monitor" 2012, 8 pages.
Radio Frequency Identification RFID, AIM Inc. White Paper, Document Version 1.2, pp. 1-17 (2001).
Request for Continued Examination (RCE) received for U.S. Appl. No. 17/531,271, mailed on Apr. 18, 2023.
Request for Continued Examination (RCE) received for U.S. Appl. No. 17/531,271, mailed on Feb. 9, 2023.
Request for Continued Examination (RCE) received for U.S. Appl. No. 17/531,271, mailed on Nov. 23, 2022.
Request for Continued Examination (RCE) received for U.S. Appl. No. 17/531,271, mailed on Sep. 19, 2022.
Request for Continued Examination (RCE) received for U.S. Appl. No. 18/183,773, mailed on May 30, 2024.
Response After Final Action received for U.S. Appl. No. 18/666,331, mailed on 11/117/2024.
Response to Non-Final Office Action received for U.S. Appl. No. 14/629,447, mailed on Nov. 6, 2017.
Response to Non-Final Office Action received for U.S. Appl. No. 17/531,271, mailed on Jun. 28, 2022.
Response to Non-Final Office Action received for U.S. Appl. No. 18/183,773, mailed on Feb. 6, 2024.
Rivest, R.L., et al., A Method for Obtaining Digital Signatures and Public-Key Cryptosystems, Laboratory for Computer Science, Massachusetts Institute of Technology.
Schaupp, L, Direct access to interstitial fluid in adipose tissue in humans by use of open- flow microperfusion, downloaded from journals.physiology.org/journal/ajpendo on Oct. 4, 2021.
Seymour, Burch, et al., Bluetooth Master/Slave Communications and Sniff/Sniff Sub- rating Modes White Paper, Aug. 14, 2008.
Sola-Gazagnes, et al., "Emergent technologies applied to diabetes: What do we need to integrate continuous glucose monitoring into daily practice? Where the long-term use of continuous glucose monitoring stands in 2011", Diabetes & Metabolism, vol. 37, pp. S65-S70 (2011).
Specification of the Bluetooth System, Experience More, Master Table of Contents & Compliance Requirements, 134 pages (Jun. 2010).
Specification of the Bluetooth System, Experience More, Specification vol. 0, Covered Core Package Version: 4.0, 41 pages (2010).
Specification of the Bluetooth System, Version 4.0 [vol. 0] 2010.
Specification of the Bluetooth System, Version 4.1 [vol. 0] 2013.
Specification of the Bluetooth System, Version 4.2 [vol. 0] 2014.
Specification of the Bluetooth System, Wireless connections made easy, Master Table of Contents & Compliance Requirements, 92 pages (Nov. 2003).
Specification of the Samsung Galaxy Alpha, Samsung Newsroom Deutschland—htt12://www.samsung.de/galaxyal12ha, 6 pages, Aug. 13, 2014 (with an English Abstract).
Stallings, William, Cryptography and Network Security Principles and Practice, Prentice Hall, 5.SUP.th .Edition.
Strickland, Ray, et al., Bluetooth Continuous Glucose Monitory Profile, Bluetooth Special Interest Group, v1.0.1, Dec. 15, 2015.
Strommer et al., "Application of Near Field Communication for Health Monitoring in Daily Life," Proceedings of the 28th IEEE FrC09. I EMBS Annual International Conference New York City, USA, 3246-3249, Aug. 30-Sep. 3, 2006.
The New Shorter Oxford English Dictionary, p. 50.
Townsend et al., "Getting Started with Bluetooth Low Energy - Tools and Techniques for Low-Power Networking," O'Reilly Media, Inc, 180 pages (2014).
Townsend, Kevin, et al., Getting Started with Bluetooth Low Energy, www.allitebooks. com.
Translation of German Infringement Complaint dated Sep. 9, 2021.
U.S. Appl. No. 14/629,447 (U.S. Pat. No. 9,913,600), filed Feb. 23, 2010 (Mar. 13, 2018).
U.S. Appl. No. 15/916,255 (U.S. Pat. No. 10,856,785), filed Mar. 8, 2018 (Dec. 8, 2020).
U.S. Appl. No. 60/614,683, filed Sep. 30, 2004, by Brister, et al.
UPC Annex A34-Second Expert Opinion of Dr. Michael Schoemaker, Exhibits MS-5 to MS-8, Nov. 8, 2024 (43 pgs.).
UPC Court of Appeal, Feb. 26, 2024, 335/2023, 38 pgs.
UPC Exhibit MS-5 to Second Expert Opinion of Dr. Michael Schoemaker, Nov. 8, 2024 (9 pgs.).
UPC Exhibit MS-6 to Second Expert Opinion of Dr. Michael Schoemaker, Nov. 8, 2024, Part 1 (63 pgs.).
UPC Exhibit MS-7 to Second Expert Opinion of Dr. Michael Schoemaker, Nov. 8, 2024 (44 pgs.).
UPC Exhibit MS-8 to Second Expert Opinion of Dr. Michael Schoemaker, Nov. 8, 2024 (25 pgs.).
Wang et al."A Feasible IMD Communcation Protocol Security without Obscurity," School of Engineering and Computing Sciences, NYIT Research Experience for Undergraduates (REU), May 26-Jul. 30, 2015, 1 page.
"Encryption and Authentication Overview", Bluetooth Specification, Version 4.0, vol. 6, 1 page (2010).
"RFID Handbook: Fundamentals and Applications in Contactless Smart Cards and Identification", Second Edition, Klaus Finkenzeller, 114 pages (2003).
"Setting Your Sensor Settings" retrieved from https://web.archive.org/web/20160803065621/http://www.medtronicdiabetes.com:80/customer-support/device-setting-and-features/sensor-settings/setting-sensor-settings on Sep. 4, 2025, 8 pages.
"Within Definition & Meaning" retrieved from "https://www.dictionary.com/browse/within" on Feb. 3, 2026, 5 pages.
A Dictionary of Computer Science for "authentication", Seventh Edition, Oxford University Press, 3 pages (2016).

(56) References Cited

OTHER PUBLICATIONS

Amendment After Non-Final Rejection received for U.S. Appl. No. 18/666,331, mailed on Sep. 24, 2024.
BBC News, Technology, Bluetooth rival unveiled by Nokia, 2 pgs. (Oct. 4, 2006).
Bloodborne pathogens, Occupational Safety and Health Admin., Labor, 29 CFR Ch. XVII (Jul. 1, 03 Edition)§ 1910.1030, pp. 260-273.
Bluetooth Specification V 2.1, Jul. 26, 2007, pp. 1-541.
Bluetooth Specification V 2.1, Jul. 26, 2007, pp. 542-906.
Bluetooth Specification, Version 4.0, 2,303 pages (2010).
Breen, The iPhone Pocket Guide, Sixth Edition, Peachpit Press, 96 pages (2012).
Burge, M, et al. "Continuous Glucose Monitoring: The Future of Diabetes Management", Diabetes Spectrum, vol. 21 (2), 2008, 9 pages.
Burr, et al., Electronic Authentication Guideline, NIST Special Publication 800-63-2, Computer Security, NIST National Institute of Standards and Technology, U.S. Department of Commerce, 123 pages (2013).
Chuang et al., "Pilot Studies of Transdermal Continuous Glucose Measurement in Outpatient Diabetic Patients and in Patients during and after Cardiac Surgery," Journal of Diabetes Science and Technology, 595-602 (2008).
Compare Specification—Apple iPhone 6 vs. Apple iphone 6 Plus—https://www.gsmarena.com/compare.php3? idPhone1=6378&idPhone2=06665, 2 pages, Jan. 31, 2022.
Complaint, "*Abbott Diabetes Care, Inc* v. *Dexcom, Inc* ", filed Aug. 11, 2005.
Complaint, Amended, "*Abbott Diabetes Care, Inc* v. *Dexcom, Inc* ", filed Jun. 27, 2006.
Cornelius, Cory, "Usable Security for Wireless Body-Area Networks" (2013). Dartmouth College PhD Dissertations. 42.
Cunningham, David and Stenken, Julie, In Vivo Glucose Sensing, Chemical Analysis, vol. 174 (2010).
Custodio et al., "A Review on Architectures and Communications Technologies for Wearable Health-Monitoring Systems," Sensors 12, 13907-13946 (2012).
Dartmouth Library, Email Confirmation re availability of PhD thesis "Usable Security for Wireless Bod-Area Networks" by C. Cory.
Declaration of Dr. Sayfe Kiael, Ph.D., Inter Partes Review of U.S. Pat. No. 10,375,222, 100 pages (2024).
Declaration of Lane Desborough, Petition for Inter Partes Review of U.S. Pat. No. 11,213,204, IPR2024-00853, 150 pages, May 3, 2024.
Desalvo et al., "Remote Glucose Monitoring in Camp Setting Reduces the Risk of Prolonged Nocturnal Hypoglycemia," Diabetes Technology & Therapeutics, vol. 16, No. 1, 10 pages, DOI: 10.1089/dia.2013.0139 (2014).
Dexcom G4® Platinum, Continuous Glucose Monitoring System, User's Guide, Dexcom, Inc, 161 pages (2015).
Dexcom G5 Mobile Continuous Glucose Monitoring System, Advisory Committee Briefing Materials, Clinical Chemistry and Clinical Toxicology Devices Panel, 283 pages (2016).
Dexcom GS User Guide, Dexcom, Inc., 265 pages (2015).
Dexcom GS™ Mobile, Continuous Glucose Monitoring System, User Guide, Dexcom, Inc, 264 pages (2015).
Dexcom News Releases—FDA Approves Dexcom G4 Platinum Continuous Glucose Monitoring System with Share—https://www.dexcom.com/en-us/news/fda-approves- dexcom-g4-platinum-continuous-glucose-monitoring-system- share, Dexcom, Inc., 2 pages, Jan. 26, 2015.
Dexcom Press Release—FDA Approves Dexcom GS® Mobile Continuous Glucose Moni-toring System—https://www.dexcom.com/news/1257506247-fda-approves- dexcom-g5@-mobile-continuous-glucose-monitoring-system, Dexcom, Inc, 4 pages, Aug. 24, 2015.
Dexcom STS 7 Plus User's Guide, 2011, 144 pgs.
Dexcom STS 7 User Guide, 2007, 74 pgs.
Dexcom, Inserting Sensor, Instructions for Use, Dexcom, Inc., 2 pages (2021).
DexcomG7, Operational Manual, User Guide, Dexcom, Inc., 179 pages (2022) (with an English Abstract).
DexcomG7, Receiver: Start Here, Operational Manual, Dexcom, Inc., 8 pages (2022).
DexcomG7, Start Here, Operational Manual, Dexcom, Inc. 9 pages (2022) (with an English Abstract).
Diallo, A.S., et al., "A Secure Authentication Scheme for Bluetooth Connection", 5th International Conference on Computer & Communication Engineering (2014).
Diglas et al., "Reduced pain perception with Pen Mate™ an automatic needle insertion device for use with an insulin pen," Practical Diabetes Int 16(2):39-41 (1999).
Electronic Authentication Guide, 123 pgs. (Aug. 2013).
Ellmerer, Martin, "Measurement of interstitial albumin in human skeletal muscle and adipose tissue by open-flow microperfusion", Am. J. Physiol Endocrinol. Metab. 278: E352-E356 (2000).
Encyclopedia Britannica, Science & Tech, Bluetooth Definition, 5 pages, (Oct. 14, 2023).
Evans, et al., "Clinical temperature acquisition using proximity telemetry", J. Biomed. Eng., 13:83-86 (1991).
Ex. 2001—A Dictionary of Computer Science, 7th edition, definition of "authentication", 3 pgs. (2016).
Excerpts from the "German Health Report Diabetes 2023" of the German Diabetes Society, Nov. 14, 2022, 24 pgs. [with English translation].
Exhibit B-22.pdf—Opponent's Written Response in Opposition ofEP 3 730 045, Sep. 27, 2023, 43 pages.
Expert Statement of Andrew Yarde, Aug. 9, 2024, 87 pgs.
Expert Statement of Professor Pantelis Georgiou, Aug. 9, 2024, 52 pgs.
Extract from the privacy notice for LibreView, Jul. 13, 2024, 7 pgs.
Farid Dowla, "The Basics of Radio Frequency Identification (RFID) Technology", Handbook of RF & Wireless Technologies, Chapter 14, 44 pages (2004).
Wettlaufer, "Merlin.Net Automation of External Reports Verification Process," A Thesis Presented to The Faculty of California Polytechnic State University, San Luis Obispo, 53 pages, Jan. 2010.
Wikipedia page for "Analyte" retrieved from "https://en.wikipedia.org/w/index.php?title-Analyte&oldid=527866671".
Wikipedia page for "Bluetooth Low Energy" retrieved from "https://en.wikipedia.org/w/index.php? title=Bluetooth_Low_Energy&oldid=744163272".
Wikipedia page for "Bluetooth" retrieved from "https://en.wikipedia.org/w/index.php?title=Bluetooth&oldid=744565671".
Wikipedia page for "Challenge-response authentication" retrieved from "https://en.wikipedia.org/w/index.php? title=Challenge-response_authentication&oldid=567947229".
Wikipedia page for "Digital signature" retrieved from "https://en.wikipedia.org/w/index.php? title=Digital_signature&oldid_523528508".
Wikipedia page for "In vivo" retrieved from https://en.wikipedia.org/w/index.php?title=In_vivo&oldid-524960105.
Wikipedia page for "Near-field communication" retrieved from "https://en.wikipedia.org/w/index.php?title=Near- field_communication&oldid=525308529".
Wikipedia page for "RSA (cryptosystem)" retrieved from "https://en.wikipedia.org/w/index.php?title=RSA_ (cryptosystem)&oldid-582212268".
Wikipedia, The Free Encyclopedia, "Continuous glucose monitor", retrieved from https://en.wikipedia.org/w/index.php? title=Continuous glucose monitor&oldid=1180606 331, 10 pages (Oct. 1, 2023).
Wikipedia, The Free Encyclopedia, "Radio-frequency identification", retrieved from https://en.wikipedia.org/wiki/Radio-frequency identification, 30 pages (Oct. 23, 2023).
Youbok Lee, "RFID Coil Design", Microchip Technology Inc, DS00678B, pp. 1-19 (1998).
Zhang et al., "Bluetooth Low Energy for Wearable Sensor-based Healthcare Systems," 2014 Health Innovations and Point-of-Care Technologies Conference Seattle, Washington USA, 251-254, Oct. 8-10, 2014.
Feature-by-Feature comparison of claims 1 and 5 ofEP921 in relation to D2 and D3, Nov. 12, 2024, 7 pgs.

(56) References Cited

OTHER PUBLICATIONS

Ferro, et al., "Bluetooth and Wi-fi Wireless Protocols: A Survey and a Comparison", IEEE Wireless Communications, 12(1):12-26 (2005).
Ferro, et al., "Bluetooth and Wi-fi Wireless Protocols: A Survey and a Comparison", IEEE Wireless Communications, pp. 1-24 (2004).
File History of U.S. Pat. No. 10,375,222, issued Aug. 6, 2019, 442 pages.
File History of U.S. Pat. No. 11,213,204 issued Jan. 1, 2022, 848 pages.
File History of U.S. Pat. No. 9,801,541 issued Oct. 31, 2017, 834 pages.
File wrapper of U.S. Appl. No. 60/587,787, filed Jul. 13, 2004, 69 pages.
Final Rejection received for U.S. Appl. No. 18/666,331, mailed on Oct. 9, 2024.
Finkenzeller, "RFID Handbook: Fundamentals and Applications in Contactless Smart Cards, Radio Frequency Identification and Near-Field Communication", Third Edition, 4 pages (2010).
FreeStyle Libre Flash Glucose Monitoring System, User's Manual, Abbott Diabetes Care Ltd., 124 pages (2014).
FreeStyle Libre Flash Glucose Monitoring System, User's Manual, Abbott Diabetes Care Ltd., 126 pages (2017).
FreeStyle Navigator Continuous Glucose Monitoring System, User Guide, Abbott Diabetes Care Inc., 195 pages (2008).
FreeStyle Navigator Continuous Monitoring System, Summary of Safety and Effectiveness Data in support of Pre-Market Approval (PMA) No. P980022, Abbott Diabetes Care, 25 pages (1999).
German Infringement Complaint dated Jul. 15, 2021.
German Infringement Complaint Service addressed to Dexcom Deutschland GmbH.
Gomez, Carles, et al., Overview an Evaluation of Bluetooth Low Energy: An Emerging Low-Power Wireless Technology, Sensors (12) 2012.
Guardian Real Time User Guide, 2006, 181 pgs.
Guder, W.G., et al., Samples: From the patient to the Laboratory, 3rd revised edition 2003.
Hamblen, "A short history of NFC: Where Near Field Communication has come from.", 2 pages, Dec 19, 2012.
Heller, A, et al., "Electrochemical Glucose Sensors and Their Applications in Diabetes Management", Chemical Reviews, 2008, pp. 2482-2505.
Higson, S.P.J. and Vadgama, P.M., Biosensors: a viable monitoring technology? Med & Biol. Eng. & Comput., 1994, 32, 601-609.
Hirsch, "Realistic Expectations and Practical Use of Continuous Glucose Monitoring for the Endocrinologist," J Clin Endocrinol Metab 94:2232-2238 (2009).
Hughes, "The Business of Self-Monitoring of Blood Glucose: A Market Profile," Journal of Diabetes Science and Technology, 3(5):1219-1223 (2009).
IEEE 100, The Authoritative Dictionary of IEEE Standards Terms for "authentication", Seventh Edition, Standards Information Network IEEE Press, 3 pages (2000).
In vitro diagnostic test systems—Requirements for blood-glucose monitoring systems for self-testing in managing diabetes mellitus, European Standard, ISO 15197, 44 pages, 2003.
Issue Fee Payment received for U.S. Appl. No. 14/629,447, mailed on Jan. 16, 2018.
Issue Fee Payment received for U.S. Appl. No. 17/531,271, mailed on May 4, 2023.
Keith-Hynes et al., "The Diabetes Assistant: A Smartphone-Based System for Real-Time Control of Blood Glucose," Electronics, 3, 609-623; doi:10.3390/electronics3040609 (2014).
Kluch, et al."Inflammation and Glucose Sensors: Use of Dexamethasone to Extend Glucose Sensor Function and Life Span in Vivo", Journal of Diabetes Science and Technology, 1(4):496-504 (2007).
Liang, et al., "An implantable bi-directional wireless transmission system for transcutaneous biological signal recording", Physiological Measurement, 26:83-97 (2005).
LibreLinkUp User Guide, Dec. 12, 2023, 28 pgs.
McCartney et al., "In vivo glucose sensing for diabetes management: progress towards non-invasive monitoring," BMJ, vol. 319, 4 pages (1999).
McDaniels, D., et al., "Remote Management of Cardiac Patients: The Forefront of a New Standard" Modern Healthcare, 2011, 6 pages.
Microchip, microID® 13.56 MHz RFID, System Design Guide, Microchip Technology Inc, 214 pages (2004).
Mohanty and Kougianos, Biosensors: A tutorial review, IEEE Potentials, pp. 35-46 (2006).
Moore, "The Potential Use of Radio Frequency Identification Devices for Active Monitoring of Blood Glucose Levels," Journal of Diabetes Science and Technology 3(1):180-183 (2009).
Morak et al., "Design and Evaluation of a Telemonitoring Concept Based on NFC- Enabled Mobile Phones and Sensor Devices," IEEE Transactions on Information Technology in Biomedicine, Nov. 2011, 8 pgs.
Mosa et al., "A Systematic Review of Healthcare Applications for Smartphones," BMC Med Informatice and Secision Making, 32 pages (2012).
MySentryTM User Guide, Medtronic Minimed, 2010, 80 pages.
Near Field Communication (NFC) Technology and Measurements, White Paper, Rohde & Schwarz, 1 page (2011).
Near Field Communication (NFC) Technology and Measurements, White Paper, Rohde & Schwarz, 18 pages (2011).
Newton, Newton's Telecom Dictionary, 30th Upldated, Expanded, Aniversry Ed., "authenticate", 4 pages (2016).
NFC Forum Bluetooth Special Interest Group, Bluetooth® Secure Simple Pairing Using NFC, 39 pages (2014).
Non-Final Office Action received for U.S. Appl. No. 17/531,271, mailed on Mar. 28, 2022.
Non-Final Rejection received for U.S. Appl. No. 18/666,331, mailed on Aug. 14, 2024.
Notice of Allowance and Fees Due received for U.S. Appl. No. 18/666,331, mailed on Nov. 20, 2024.
Notice of Allowance received for U.S. Appl. No. 17/531,271, mailed on Dec. 21, 2022.
Notice of Allowance received for U.S. Appl. No. 17/531,271, mailed on Feb. 23, 2023.
Notice of Allowance received for U.S. Appl. No. 17/531,271, mailed on Jul. 25, 2022.
Notice of Allowance received for U.S. Appl. No. 17/531,271, mailed on May 2, 2023.

* cited by examiner

ANALYTE MONITORING AND MANAGEMENT DEVICE AND METHOD TO ANALYZE THE FREQUENCY OF USER INTERACTION WITH THE DEVICE

RELATED APPLICATIONS

The present application is a continuation of U.S. patent application Ser. No. 15/916,255 filed Mar. 8, 2018, which is a continuation of U.S. patent application Ser. No. 14/629,447 filed Feb. 23, 2015, now U.S. Pat. No. 9,913,600, which is a continuation of U.S. patent application Ser. No. 13/448,287 filed Apr. 16, 2012, which is a continuation of U.S. patent application Ser. No. 12/147,464 filed Jun. 26, 2008, now U.S. Pat. No. 8,160,900, which claims priority under § 35 U.S.C. 119(e) to U.S. Provisional Application No. 60/947,026 filed Jun. 29, 2007 entitled "Analyte Monitoring and Management Device and Method to Analyze the Frequency of User Interaction with the Device," the disclosures of each of which are incorporated by reference for all purposes.

BACKGROUND

The detection of the level of analytes, such as glucose, lactate, oxygen, and the like, in certain individuals, is vitally important to their health. For example, the monitoring of glucose is particularly important to individuals with diabetes. Diabetics may need to monitor glucose levels to determine when insulin is needed to reduce glucose levels in their bodies or when additional glucose is needed to raise the level of glucose in their bodies.

A conventional technique used by many diabetics for personally monitoring their blood glucose level includes the periodic drawing of blood, the application of that blood to a test strip, and the determination of the blood glucose level using colormetric, electrochemical, or photometric detection. This technique does not permit continuous or automatic monitoring of glucose levels in the body, but typically must be performed manually on a periodic basis. Unfortunately, the consistency with which the level of glucose is checked varies widely among individuals. Many diabetics find the periodic testing inconvenient and they sometimes forget to test their glucose level or do not have time for a proper test.

In vivo glucose sensors that continuously or automatically monitor the individual's glucose level and enable individuals to more easily monitor their glucose, or other analyte levels are also commercially available. These systems may provide the user with accurate analyte levels at ten, five or even one minute intervals. Some examples of such systems are illustrated in U.S. Pat. No. 6,175,752, and in U.S. Patent Publication No. 2004/0186365 filed Dec. 26, 2003, now U.S. Pat. No. 7,811,231, entitled "Continuous Glucose Monitoring System and Methods of Use." Devices and systems for management of the analyte level may also be included in the analyte monitoring system. An example of an analyte management system is an insulin pump, which may manage the analyte level by, for example, delivering a dose of insulin to the user in response to the glucose levels of the user. The analyte management system may be automatic, user controlled, or any combination thereof.

Clinical studies have shown that some patients derive considerable benefits from an increased frequency of available analyte levels, a benefit provided by the analyte measuring systems. However, other patients derived little or no benefit from an increased availability of analyte levels. Using glucose monitoring as an example, patients who derived little or no value from the glucose monitoring systems were at an increased risk of hyperglycemic or hypoglycemic episodes.

Increasingly, research has associated the lack of frequent interaction with the analyte monitoring system as the reason that some patients potentially derive reduced value from the analyte monitoring systems. As a result, there is a need for a system which reminds or encourages the user to interact with the analyte monitoring system at a minimum frequency.

SUMMARY

Exemplary embodiments of the present disclosure overcome the above disadvantages and other disadvantages not described above and provide advantages which will be apparent from the following description of exemplary embodiments of the disclosure. Also, the present disclosure is not required to overcome the disadvantages described above.

According to one aspect of the present disclosure, there is provided methods to analyze user interaction with a medical device. Exemplary embodiments include methods to encourage user interaction with a medical device that may include monitoring a user's actual frequency of interaction with the medical device; comparing the user's actual frequency of interaction with the medical device to at least one predetermined target level of interaction; and alerting the user when the user's actual frequency of interaction with the medical device is equal to or below the at least one predetermined target level of interaction.

According to one aspect of the present disclosure, the user may be informed of the difference between the actual frequency of interaction with the medical device and the predetermined target level of interaction.

According to one aspect of the present disclosure the user may be alerted using an alarm. The alarm may be an audible and/or visual and/or vibrating alarm. According to another aspect of the present disclosure, the audible alarm may increase in loudness over time after being activated.

According to one aspect of the present disclosure the method may include a plurality of predetermined target levels of interaction, wherein alerting the user distinguishes between the plurality of target levels of interaction.

According to one aspect of the present disclosure, the user may be required to perform at least one step to turn off the alert. According to yet another aspect, the at least one step may be a decision related to the user's state of health.

According to one aspect of the present disclosure, the at least one predetermined target level of interaction may be adjusted by an authorized user. The at least one predetermined target level of interaction may also be adjusted according to a time of day, type of activity, or projected future analyte level.

According to another aspect of the present disclosure, the history of the user's actual frequency of interaction with the medical device may be recorded. In this aspect, the at least one predetermined target level of interaction may be adjusted according to the recorded history. Moreover, the history of the user's actual frequency of interaction with the medical device may be organized according to behavior variables inputted by the user. According to another aspect of the present disclosure, the at least one predetermined target level of interaction may be adjusted according to a data received from a sensor located on the user.

According to one aspect of the present disclosure, the user may be rewarded when the actual frequency of interaction stays above the at least one predetermined level of interaction for a predetermined time.

According to another aspect of the present disclosure, there is disclosed an analyte monitoring apparatus comprising a sensor which is attached to a user for monitoring an analyte level of the user, the sensor further comprising a transmitter which transmits information obtained by the sensor; and a receiver unit comprising a receiver for receiving data from the sensor, and a display coupled to the receiver which displays the received data to the user when the user interacts with the receiver unit, wherein the receiver unit monitors the user's actual frequency of interaction with the device, compares the user's actual frequency of interaction with the receiver unit to at least one predetermined target level of interaction, and alerts the user when the user's actual frequency of interaction with the receiver unit is equal to or below the at least one predetermined target level of interaction.

BRIEF DESCRIPTION OF THE DRAWINGS

The above and other features and advantages of the present disclosure will become more apparent from detailed exemplary embodiments set forth hereinafter with reference to the attached drawings in which.

DETAILED DESCRIPTION

Figure 1:
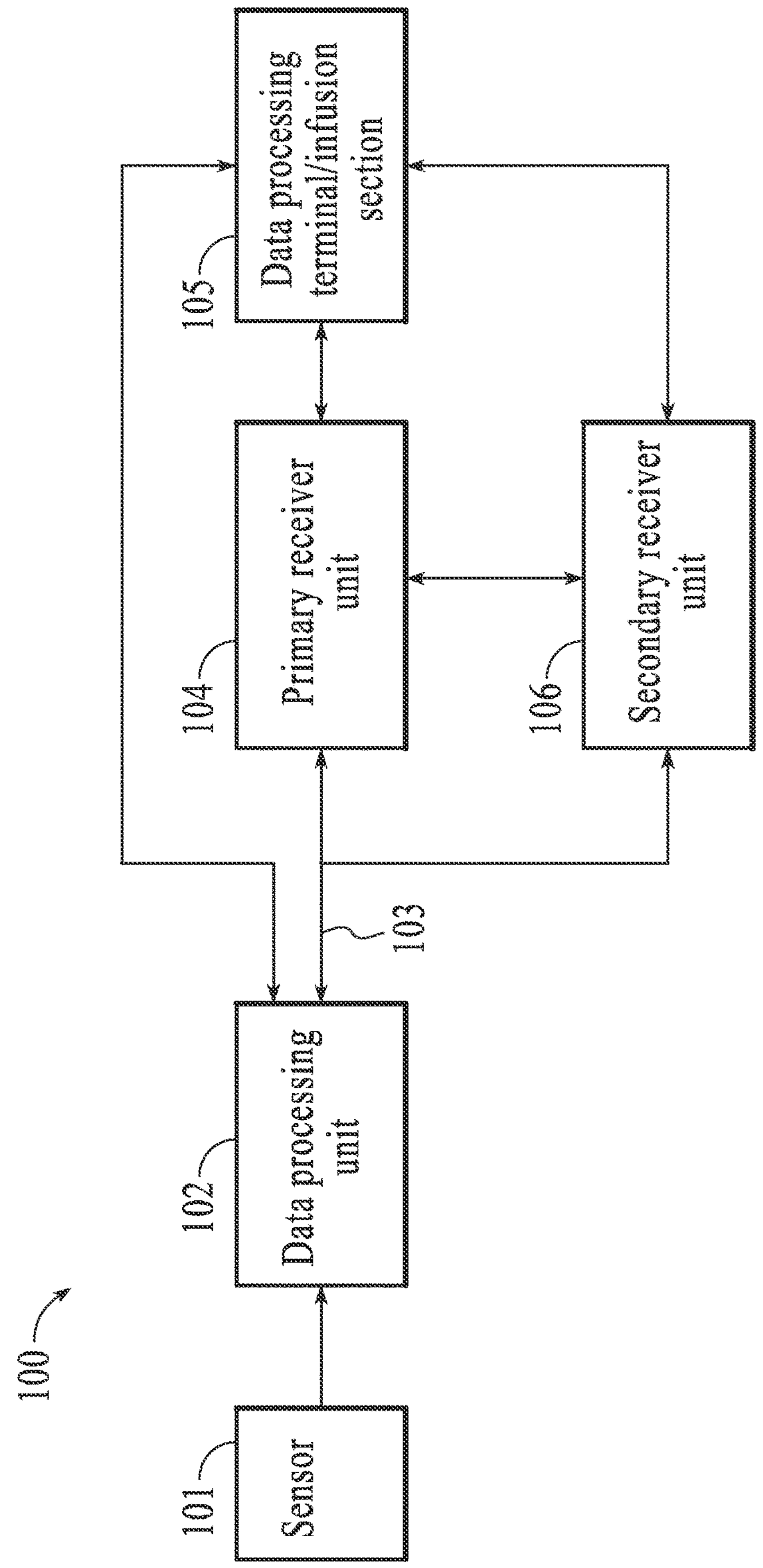
FIG. 1 is a block diagram of an exemplary embodiment of a data monitoring and management system according to the present disclosure.

The present disclosure will now be described more fully with reference to the accompanying figures, in which exemplary embodiments of the disclosure are shown. The figures shown herein are not necessarily drawn to scale, with some components and features being exaggerated for clarity. Like reference numerals in the figures denote like elements.

It is also to be understood that the terminology used herein is for the purpose of describing particular embodiments only, and is not intended to be limiting, since the scope of the present disclosure will be limited only by the appended claims. Unless defined otherwise, all technical and scientific terms used herein have the same meaning as commonly understood by one of ordinary skill in the art to which this disclosure belongs. It must be noted that as used herein and in the appended claims, the singular forms "a," "an," and "the" include plural referents unless the context clearly dictates otherwise.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Embodiments are described herein generally with respect to in vivo analyte monitoring device and methods in which at least a portion of an analyte sensor is positioned beneath a skin surface of a user, where such description is not intended to limit the scope of the disclosure in any way. Also contemplated are in vitro analyte monitoring systems, e.g., small volume (e.g., sample volumes ranging from about 0.1 to about 1 microliter), and/or short assay times (e.g., assay times ranging from about 1 second to about 10 seconds). In vitro systems usually include a test strip and a meter to read the test strip. Examples of in vitro analyte systems include, but are not limited to, FreeStyle® and Precision® blood glucose monitoring systems from Abbott Diabetes Care Inc. Also contemplated are integrated systems in which one or more components of an in vitro system are included in a single housing, e.g., lance, test strip or meter.

FIG. 1 shows a data monitoring and management system such as, for example, an analyte (e.g., glucose) monitoring system 100 in accordance with certain embodiments. Embodiments of the subject disclosure are further described primarily with respect to glucose monitoring devices and systems, and methods of glucose detection, for convenience only and such description is in no way intended to limit the scope of the disclosure. It is to be understood that the analyte monitoring system may be configured to monitor a variety of analytes at the same time or at different times.

Additionally, in one exemplary embodiment the analyte monitoring system may include an analyte management system, such as an insulin pump. Thus, it is to be understood that the following description is directed to an analyte (for example, glucose) monitoring system for convenience only and such description is in no way intended to limit the scope of the disclosure.

Analytes that may be monitored include, but are not limited to, acetyl choline, amylase, bilirubin, cholesterol, chorionic gonadotropin, creatine kinase (e.g., CK-MB), creatine, creatinine, DNA, fructosamine, glucose, glutamine, growth hormones, hormones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those exemplary embodiments that monitor more than one analyte, the analytes may be monitored at the same or different times.

Moreover, the description herein is directed primarily to electrochemical sensors for convenience only and is in no way intended to limit the scope of the disclosure. Other sensors and sensor systems are contemplated. Such include, but are not limited to, optical sensors, colorimetric sensors, and sensors that detect hydrogen peroxide to infer analyte levels, etc.

Referring to FIG. 1, the analyte monitoring system 100 includes a sensor 101, a data processing unit 102 connectable to the sensor 101, and a primary receiver unit 104, which is configured to communicate with the data processing unit 102 via a communication link 103. In certain embodiments, the primary receiver unit 104 may be further configured to transmit data to a data processing terminal 105 to evaluate or otherwise process or format data received by the primary receiver unit 104. The data processing terminal 105 may be configured to receive data directly from the data processing unit 102 via a communication link which may optionally be configured for bi-directional communication. Further, the data processing unit 102 may include a transmitter or a transceiver to transmit and/or receive data to and/or from the primary receiver unit 104 and/or the data processing terminal 105 and/or optionally the secondary receiver unit 106. In one exemplary embodiment, the primary receiver unit 104 may be designed to sit on a shelf or nightstand. In this exemplary embodiment, the primary receiver unit 104 may be used by parents to monitor their children while they sleep or to awaken patients during the night. In addition, in this exemplary embodiment the primary receiver unit may include a lamp or a radio for convenience and/or for activation as an alarm.

Also shown in FIG. 1 is an optional secondary receiver unit 106 which is operatively coupled to the communication link and configured to communicate with the data processing unit 102. The secondary receiver unit 106 may also be configured to communicate with the primary receiver unit 104, as well as the data processing terminal 105. The secondary receiver unit 106 may be configured for bi-directional wireless communication with each of the data processing unit 102, the primary receiver unit 104 and the data processing terminal 105. In certain embodiments the secondary receiver unit 106 may be a de-featured receiver as compared to the primary receiver, i.e., the secondary receiver may include a limited or minimal number of functions and features as compared with the primary receiver unit 104. As such, the secondary receiver unit 106 may include a smaller (in one or more, including all, dimensions) compact housing or be embodied in a device such as a wrist watch, arm band, etc., for example. Alternatively, the secondary receiver unit 106 may be configured with the same or substantially similar functions and features as the primary receiver unit 104. The secondary receiver unit 106 may also include a docking portion to be mated with a docking cradle unit for placement by, e.g., the bedside for night time monitoring, and/or a bi-directional communication device. A docking cradle may recharge a power supply.

Only one sensor 101, data processing unit 102 and data processing terminal 105 are shown in the embodiment of the analyte monitoring system 100 illustrated in FIG. 1. However, it will be appreciated by one of ordinary skill in the art that the analyte monitoring system 100 may include more than one sensor 101, and/or more than one data processing unit 102, and/or more than one data processing terminal 105. Multiple sensors may be positioned in a patient for analyte monitoring at the same or different times. In certain embodiments, analyte information obtained by a first positioned sensor may be employed as a comparison to analyte information obtained by a second sensor. This may be useful to confirm or validate analyte information obtained from one or both of the sensors. Such redundancy may be useful if analyte information is contemplated in critical therapy-related decisions. In certain embodiments, a first sensor may be used to calibrate a second sensor, or vice-versa.

The analyte monitoring system 100 may be a continuous monitoring system, or semi-continuous, or a discrete monitoring system. In a multi-component environment, each component may be configured to be uniquely identified by one or more of the other components in the system so that communication conflict may be readily resolved between the various components within the analyte monitoring system 100. For example, unique IDs, communication channels, and the like, may be used.

In certain embodiments, the sensor 101 is physically positioned in or on the body of a user whose analyte level is being monitored. The sensor 101 may be configured to at least periodically sample the analyte level of the user and convert the sampled analyte level into a corresponding signal for transmission by the data processing unit 102. The data processing unit 102 performs data processing functions, where such functions may include, but are not limited to, filtering and encoding of data signals, each of which corresponds to a sampled analyte level of the user, for transmission to a receiver unit (104 or 106) via the communication link 103. In certain embodiments, one or more application-specific integrated circuits (ASIC) may be used to implement one or more functions or routines associated with the operations of the data processing unit (and/or receiver unit) using for example one or more state machines and buffers.

In one embodiment, the sensor 101 or the data processing unit 102 or a combined sensor/data processing unit may be wholly implantable under the skin layer of the user.

In certain embodiments, the primary receiver unit 104 may include an analog interface section including an RF receiver and an antenna that is configured to communicate with the data processing unit 102 via the communication link 103, and a data processing section for processing the received data from the data processing unit 102 such as data decoding, error detection and correction, data clock generation, data bit recovery, etc., or any combination thereof.

In operation, the primary receiver unit 104 in certain exemplary embodiments is configured to synchronize with the data processing unit 102 to uniquely identify the data processing unit 102, based on, for example, an identification information of the data processing unit 102, and thereafter, to periodically receive signals transmitted from the data processing unit 102 associated with the monitored analyte levels detected by the sensor 101.

Referring again to FIG. 1, the data processing terminal 105 may include a personal computer, a portable computer such as a laptop or a handheld device (e.g., personal digital assistants (PDAs), telephone such as a cellular phone (e.g., a multimedia and Internet-enabled mobile phone such as an iPhone or similar phone), mp3 player, pager, and the like), or a drug delivery device (e.g., an insulin pump), each of which may be configured for data communication with the receiver via a wired or a wireless connection. Additionally, the data processing terminal 105 may further be connected to a data network (not shown) for storing, retrieving, updating, and/or analyzing data corresponding to the detected analyte level of the user.

In certain embodiments, the communication link 103 as well as one or more of the other communication interfaces shown in FIG. 1, may use one or more of: a radio frequency (RF) communication protocol, an infrared communication protocol, a Bluetooth® enabled communication protocol, an 802.11x wireless communication protocol, or an equivalent wireless communication protocol which would allow secure, wireless communication of several units (for example, per HIPAA requirements), while avoiding potential data collision and interference.

Figure 2:
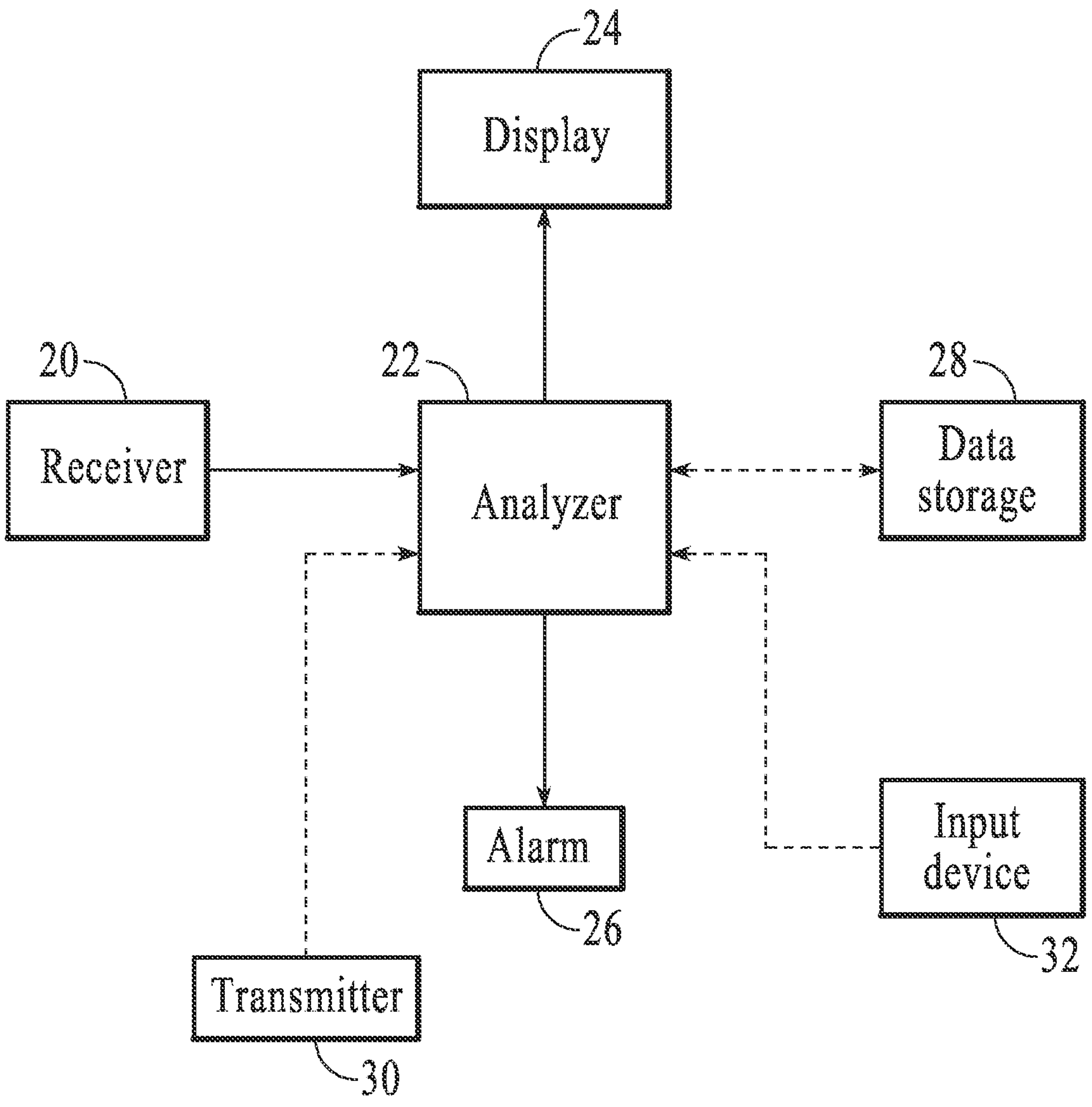
FIG. 2 is a block diagram of one exemplary embodiment of a receiver unit, according to the present disclosure.

The primary receiver unit 104, according to an exemplary embodiment of the present disclosure, illustrated in block form in FIG. 2, includes a receiver 20 to receive data from the data processing unit 102, an analyzer 22 to evaluate the data, a display 24 to provide information to the user, and an alarm system 26 to warn the user when a condition arises. The primary receiver unit 104 may also optionally include a data storage device 28, a transmitter 30, and/or an input device 32. As described above, the secondary receiver unit 106 may have the same structure as the primary receiver unit 104, and as such, the following description of receiver unit functions apply equally to the primary and secondary receiver units.

In one exemplary embodiment, a primary receiver unit 104 may be a bedside unit for use at home. The bedside unit may have its own data analyzer and data storage. The data may be communicated from the data processing unit 102 or another receiver unit, such as a secondary receiver unit 106. Thus, at least one receiver unit contains all the relevant data so that the data can be downloaded and analyzed without significant gaps.

The receiver 20 may be formed using known receiver and antenna circuitry and may be tuned or tunable to the frequency or frequency band of the data processing unit 102. In one exemplary embodiment, the receiver 20 is capable of receiving signals from a distance greater than the transmitting distance of the data processing unit 102.

In another embodiment, a repeater unit (not shown) is used to boost a signal from the data processing unit 102 so that the signal can be received by receiver units 104 and 106 that may be distant from the data processing unit 102. The repeater unit is typically independent of the data processing unit 102, but, in some cases, the repeater unit may be configured to attach to the data processing unit 102. Typically, the repeater unit includes a receiver for receiving the signals from the data processing unit 102 and a transmitter for transmitting the received signals. The transmitter of the repeater unit may be more powerful than the transmitter of the data processing unit 102 in one exemplary embodiment of the present disclosure. The repeater unit may be used, for example, in a child's bedroom for transmitting a signal from a data processing unit 102 on the child to a primary receiver unit 104 in the parent's bedroom for monitoring the child's analyte levels and frequency of interaction with the secondary receiver unit 106.

A variety of displays 24 may be used, including cathode ray tube displays (particularly for larger units), light emitting diode (LED) displays, or liquid crystal display (LCD) displays. The display 24 may be monochromatic (e.g., black and white) or polychromatic (i.e., having a range of colors). The display 24 may contain symbols or other indicators that are activated under certain conditions (e.g., an alert to the user may become visible on the display when the user's frequency of interaction with the receiver units 104 and 106 falls below the predetermined target level of interaction). The display 24 may also contain more complex structures, such as LCD or LED alphanumeric structures, portions of which can be activated to produce a letter, number, or symbol. For example, the display 24 may include region 34 to display numerically the level of the analyte, as illustrated in FIG. 3.

Figure 4:
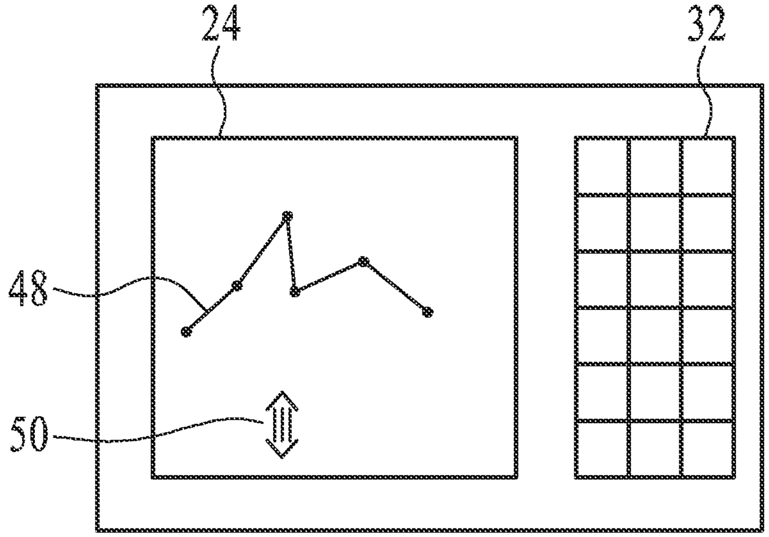
FIG. 4 is a front view of a second exemplary embodiment of a receiver unit.
Figure 5:
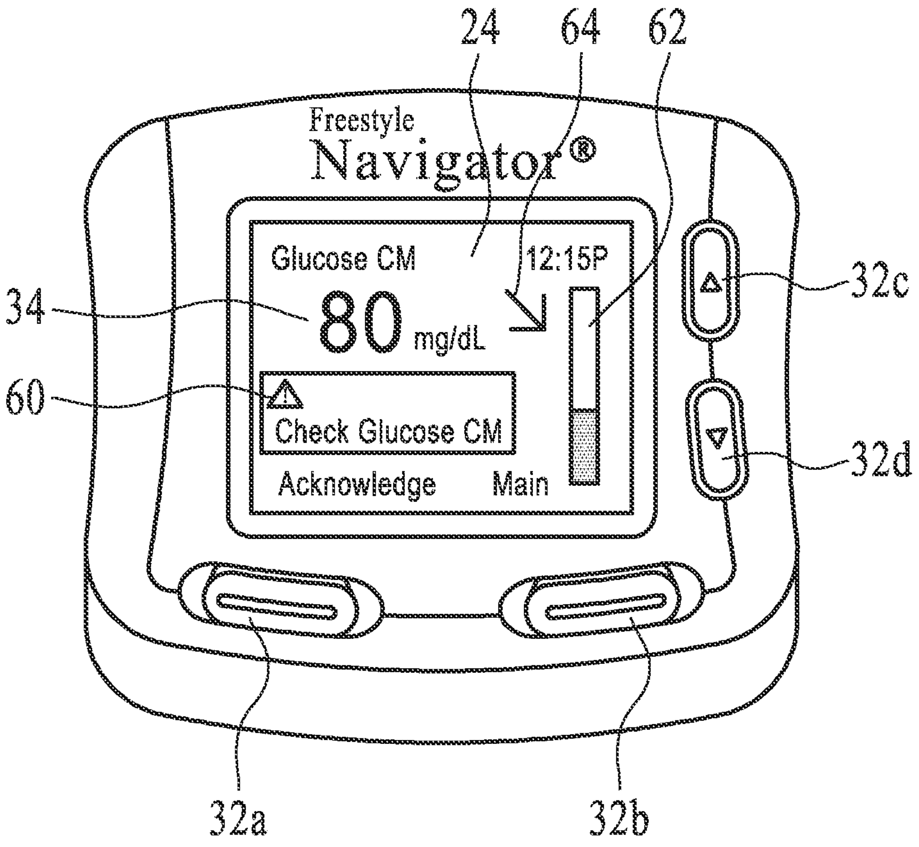
FIG. 5 is a front view of a third exemplary embodiment of a receiver unit.

In one exemplary embodiment, as shown in FIG. 5, the display 24 also provides a message 60 to the user to direct the user in an action. Such messages may include, for example, "Check Analyte Level", if the user's frequency of interaction with a receiver unit falls below the predetermined target level. In another exemplary embodiment, the messages may provide helpful hints or tips to the user. The display may also include other indicators 36, including directional arrows, etc., which may be activated under certain conditions. For example, indicator 38 of a glucose monitoring device, may be activated if the patient is hyperglycemic. Other indicators may be activated in the cases of hypoglycemia (40), impending hyperglycemia (42), impending hypoglycemia (44), a malfunction, an error condition, or when calibration of the device is required (46). In some embodiments, color coded indicators may be used. Alternatively, the portion 34 which displays the analyte concentration, may also include a composite indicator 50 (see FIG. 4), portions of which may be appropriately activated to indicate any of the conditions described above. In another exemplary embodiment, the display may be capable of displaying a graph 48 of the analyte level over a period of time, as illustrated in FIG. 4.

Figure 3:
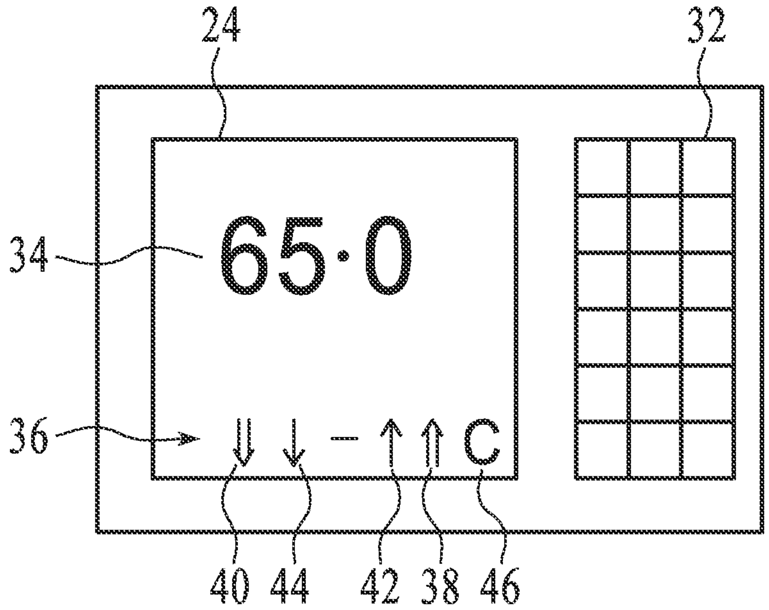
FIG. 3 is a front view of an exemplary embodiment of a receiver unit.

One example of a receiver unit (104 or 106) is illustrated in FIG. 3. The display 24 of this particular receiver unit (104 or 106) includes a portion 34 that displays the level of the analyte, for example, the blood glucose concentration. In one embodiment, the screen may be blank or dark when in the resting state. In this exemplary embodiment, the screen may be activated if the user interacts with the device. In another embodiment, the receiver unit (104 or 106) indicates the time of day on the default screen, and the user may view the current analyte level by interacting with the receiver unit (104 or 106), for example by pressing a button or the like on the receiver unit (104 or 106), which will display the current analyte level. In this way, receiver units 104 and 106 can monitor the frequency of interaction between the user and the receiver units 104 and 106.

In one exemplary embodiment, the user's interaction with the receiver units 104 and 106 is system specific. That is, the receiver units 104 and 106 update each other when the user interacts with one of the receiver units (either 104 or 106). In this embodiment, the user needs to only interact with one unit to maintain the target level of interaction.

In another embodiment, the user's interaction with the receiving units 104 and 106 may be receiver unit specific. One example where the user's interaction with the receiver is receiver unit specific may be a guardian/child relationship. In this example, the child's level of interaction (with, for example, the primary receiver unit 104) and the guardian's level of interaction (with, for example, the secondary receiver unit 106) should be assessed independently.

In another exemplary embodiment, as illustrated in FIG. 5, the display 24 may display a bar graph 62, or any other suitable indicator, comparing the user's frequency of interaction with the receiver units 104 and 106 to the predetermined target frequency. Additionally, as shown in FIG. 5, the display 24 may further be capable of displaying an analyte indicator 64, which may indicate the rate of change of the analyte, and the direction of change of the analyte, e.g., by the particular direction of an arrow or the like. In this exemplary embodiment, the analyte indicator 64 may point in different directions, such as for example, around a 360 degree clock. Other examples of graphs may include graphs of the user's frequency of interaction with the receiver unit (104 or 106), or units (104 and 106), over a period of time, and graphs of the rate of change or acceleration in the rate of change of the analyte level over time.

In some exemplary embodiments, the receiver unit is configured so that the user may choose the particular display (e.g., blood glucose concentration or graph of concentration versus time) that the user wishes to view. The user may choose the desired display mode by pushing a button or the like, for example, on an optional input device 32. When the user interacts with the device, to view or choose a particular display or to wake the device from its resting state, the receiver unit 104 or 106 may record the date and time of the user's interaction with that receiver unit. In this way, the receiver units 104 and 106 can monitor the frequency of user interaction with the receiver units. The optional input device 32 for interacting with the receiver units 104 and 106 will be described in greater detail below.

The above-described graphs benefit both the user and the health care provider ("HCP"). The user can benefit from subtle behavioral modification as the graphs and/or screen prompts encourage more frequent interaction with the device and the expected improvement in outcomes.

HCPs may benefit from more cumulative statistics (such as average glucose views per day, average glucose views before/after meals, average glucose views on "in-control"

vs. "out-of-control" days or time of day) which may be obtained from the record of user's interaction frequency with the device and which can be used to understand why a patient may not be realizing expected gains from the analyte monitoring system. If an HCP sees that a patient is not benefiting as expected from the analyte monitoring system, they may recommend an increased level of interaction (e.g., increase interaction target level).

In one exemplary embodiment, the receiver units 104 and 106 may include software. In this exemplary embodiment, each instance of user interaction, by pressing a button or the like, with a receiver unit 104 or 106, or both receiver units 104 and 106, may be recorded. The software may associate each instance of user interaction with the date and time of that interaction. For example, the software may record each instance that the user queries the main screen of the receiver unit 104 or 106. In this exemplary embodiment, the receiver unit 104 or 106 may further include an algorithm for comparing the frequency of user interaction with the receiver to a predetermined frequency of interaction. In this exemplary embodiment, if the frequency of a user's interaction with the receiver units 104 and 106 matches or falls below the predetermined level of interaction, the receiver unit (104 or 106) may alert the user through an audible or vibratory alert. The alert system will be described in greater detail below.

In another exemplary embodiment of the present disclosure, the receiver units 104 and 106 may also contain software designed to encourage interaction with the receiver units. For example, the software may set target rates for the user, so that the user strives to achieve a desired interaction frequency with the receiver unit. In another exemplary embodiment, the software may offer educational information related to treatment as well as helpful hints and tips, thereby educating the user as to the importance of maintaining a predetermined target level of interaction with the receiver unit.

In yet another embodiment, the receiver units 104 and 106 may include software that prompts user interaction, e.g., an electronic game, or cartoon-like character, or the like, that requires feedback from the user. In one exemplary embodiment, the cartoon-like character or the like may have a "health bar" or a "life bar" which would represent the level of interaction between the user and the analyte monitoring system 100. That is, by frequently interacting with the cartoon-like character, the user will keep the health, or life, level of the cartoon-like character above the predetermined target level. In one exemplary embodiment, the user may "feed" the cartoon-like character by interacting with the device. The user's analyte level, or other relevant information should also be displayed on the screen of the device during interaction between the user and the cartoon-like character. In one exemplary embodiment, the user will be limited in the amount of interaction in a predetermined time. That is, the user will not be able to front-load the amount of interaction with the device, and then ignore the device for a prolonged period of time. As such, the device may only record a predetermined number of interactions within a certain period of time.

By interacting with the cartoon-like character, the user may also be educated as to the benefits of maintaining a proper target rate of interaction with the device, or may at least stay informed as to his own state of health. This embodiment may be particularly interesting to children as it may help ensure that children maintain the necessary level of interaction with the monitoring device of this disclosure. This exemplary embodiment may also be coupled with education regarding treatment options, helpful hints and tips. Moreover, the above-described embodiment need not be used with a continuous glucose monitoring ("CGM") device.

In one exemplary embodiment of the present disclosure, the above concept can also be adapted to the "finger stick test." Using glucose as an example, the user may interact with the cartoon-like character by manually checking his blood glucose level. That is, each time the user manually checks his glucose level, using the finger stick test, the cartoon-like character may gain a point to the "health" or "life" bar. Similar to the embodiment described above, the "health" or "life" bar may represent the target level of user interaction. In this way, the user will desire to keep the cartoon-like character healthy, and thus interact with the device at an increased frequency. With regard to the embodiments described above, one of ordinary skill in the art will understand that the cartoon-like character is simply an example, and that any kind of character or figure may be used.

In order to achieve the full benefit of the analyte monitoring system 100, the user should maintain a predetermined target rate of interaction with the system. In one exemplary embodiment, the predetermined target level of user interaction is set by an HCP, or the user's health care team. Thus, each predetermined target level of interaction will likely depend on the specific user. However, in one exemplary embodiment, factors affecting the predetermined level of user interaction with the system may be: the particular analyte to be measured, the user's general state of health, (for example, more frequent during sick days), symptoms exhibited by the user, time of day, time since or until meal, activity level and other events.

In one exemplary embodiment, the target level may be programmed (or user modifiable) to vary during the course of the day or week (work week vs. weekend), with these rates being easily adjustable to account for events or changes, such as, during sick days, times of high activity, or other times when more frequent interactions should be encouraged. Although HCPs may recommend only general interaction levels (e.g., once per hour during waking hours), these levels may be tailored to the individual user. For example, if a user feels overwhelmed with CGM technology, lower target levels of interaction may be needed, whereas a user who feels empowered by the technology may be encouraged to interact with the device at a higher frequency. Generally, HCPs will review interaction levels during routine visits when assessing general health and reviewing data uploads (e.g., approximately every 3 months for patients with diabetes). However, this approach may differ depending on the user, or other factors.

In another exemplary embodiment, the predetermined target level of user interaction with the receiver units 104 and 106 may be set according to the time of day. For example, a user may interact with the receiver units 104 and 106 more frequently during the day than at night. Additionally, in another exemplary embodiment, the predetermined target level of user interaction with the receiver units 104 and 106 may be set according to the type of activity being performed by the user. For example, a user on a long-distance bicycle ride or car ride may need to check the analyte levels more frequently. In one exemplary embodiment, an HCP may recommend target levels of interaction corresponding to various events. In another exemplary embodiment, the target level of user interaction may be set by the user, or any other authorized party.

In one exemplary embodiment, the system may automatically adjust the target level of interaction based upon the user's activity level or state of general wellness. In this exemplary embodiment, the system may use pulse rate, body temperature, respiration rate or other indicators to adjust the analyte level. Alternatively, position sensors, accelerometers or the like may be used to detect sleep and reduce (or even suspend) the target interaction frequency.

In another exemplary embodiment, the analyte monitoring system 100 may use the detected analyte levels to adjust future target levels of interaction. For example, the system may use an increase in glucose level, an increase in the rate of change of the glucose level, user entered information or some other analysis of the measured analyte level to identify a need to adjust the current target level of interaction. In one exemplary embodiment, the analyte levels may detect that the user has recently had a meal and may then adjust the interaction frequency automatically to a pre-programmed or user-set level.

Another exemplary embodiment may include a plurality of predetermined target levels of user interaction with the system of the present disclosure. For example, the present disclosure may include an "ideal" level of interaction, an "acceptable" level of interaction and a "critical" level of interaction. These levels may shift based on several factors. In one exemplary embodiment, the level of interaction may be adjusted to an increased or decreased target level of interaction based upon the monitoring results, based upon some user interaction with the device (e.g., meal or activity level entry), or may be pre-programmed to vary with the time of day or day of the week. The monitoring results may include, analyte levels, the rate of change of analyte levels, etc.

In another exemplary embodiment, the interaction frequency level may be relative to the predetermined target interaction frequency. For example "ideal" may be approximately 90% or more of the target level; "acceptable" may be 70-90% of the target level; and "critical" may be below 70% of the target level.

In another exemplary embodiment of the present disclosure, the analyte monitoring system 100 may adjust the predetermined target levels of user interaction according to the condition of the user. Using glucose as an example, if the user's level of glucose drops below a certain threshold, the system may alert the user that hypoglycemia may occur. In this exemplary embodiment, the analyte monitoring system 100 may adjust the target rate of user interaction to be more frequent, thus prompting the user to interact with the device more often, and thus encourage the user to raise his level of glucose to a more acceptable level. Once the glucose level returns to an acceptable level, the system may adjust the target interaction rate accordingly.

In the above exemplary embodiment, the system may include a multiplier for adjusting target levels of user interaction, wherein the predetermined target rate of interaction is multiplied by a predetermined amount according to the condition reached. In one exemplary embodiment, a multiplier may be associated with a predetermined target level, such as for example the "critical" target level. In another exemplary embodiment, a multiplier may be associated with a specific condition, or analyte level of the user, such as when the user is in danger of becoming hypoglycemic.

In another exemplary embodiment, the system may adjust the rate of interaction according to predicted future analyte levels. For example, the analyte monitoring system 100 may predict the future analyte level of a user by monitoring the present rate of change of the user's analyte level.

As shown in FIG. 2, a receiver unit (104 or 106) may also optionally include an alarm system 26. In one exemplary embodiment, the alarm system 26 is triggered when the user's frequency of interaction with the receiver units 104 and 106 falls below a predetermined target level of interaction. In another exemplary embodiment, the alarm system 26 may be triggered when the user's level of interaction matches the predetermined target level of interaction.

The alarm system 26 may contain one or more individual alarms. Each of the alarms may be individually activated to indicate one or more predetermined target levels of user interaction with the receiver units 104 and 106. The alarms may be, for example, auditory or visual. Other sensory-stimulating alarm systems may be used, including alarm systems that direct the data processing unit 102 to heat, cool, vibrate, or produce a mild electrical shock. In some embodiments, the alarms are auditory with a different tone, note or volume indicating different predetermined target levels of user interaction with the receiver units 104 and 106. In one exemplary embodiment of the present disclosure, various tones of the alarm system 26 may indicate varying urgency levels of a user's need to interact with the receiver units 104 and 106. For example, a high volume alarm may indicate a "critical" predetermined target level being reached, while a lower volume alarm might indicate that the user's frequency of interaction has fallen below the "acceptable" level of interaction with the receiver unit. Visual alarms may also use a difference in color or brightness of the display, or indicators on the display, to distinguish between different predetermined target levels of user interaction with the receiver units 104 and 106. In some embodiments, an auditory alarm system may be configured so that the volume of the alarm increases over time until the alarm is deactivated.

In some embodiments, the alarms may be automatically deactivated after a predetermined time period. In other embodiments, the alarms may be configured to deactivate only when the user interacts with a receiver unit.

In another exemplary embodiment of the present disclosure, the receiver units 104 and 106 may include software for requiring the user to perform a series of operations in order to silence the alarm. In this exemplary embodiment, the operations may be therapeutic decision options being presented to the user, or may be a series of options related to the user's state of health. The user would then need to review these options and acknowledge understanding by interacting with the device. In certain cases, the alarm may not turn off unless the user acknowledges such understanding.

Figure 6:
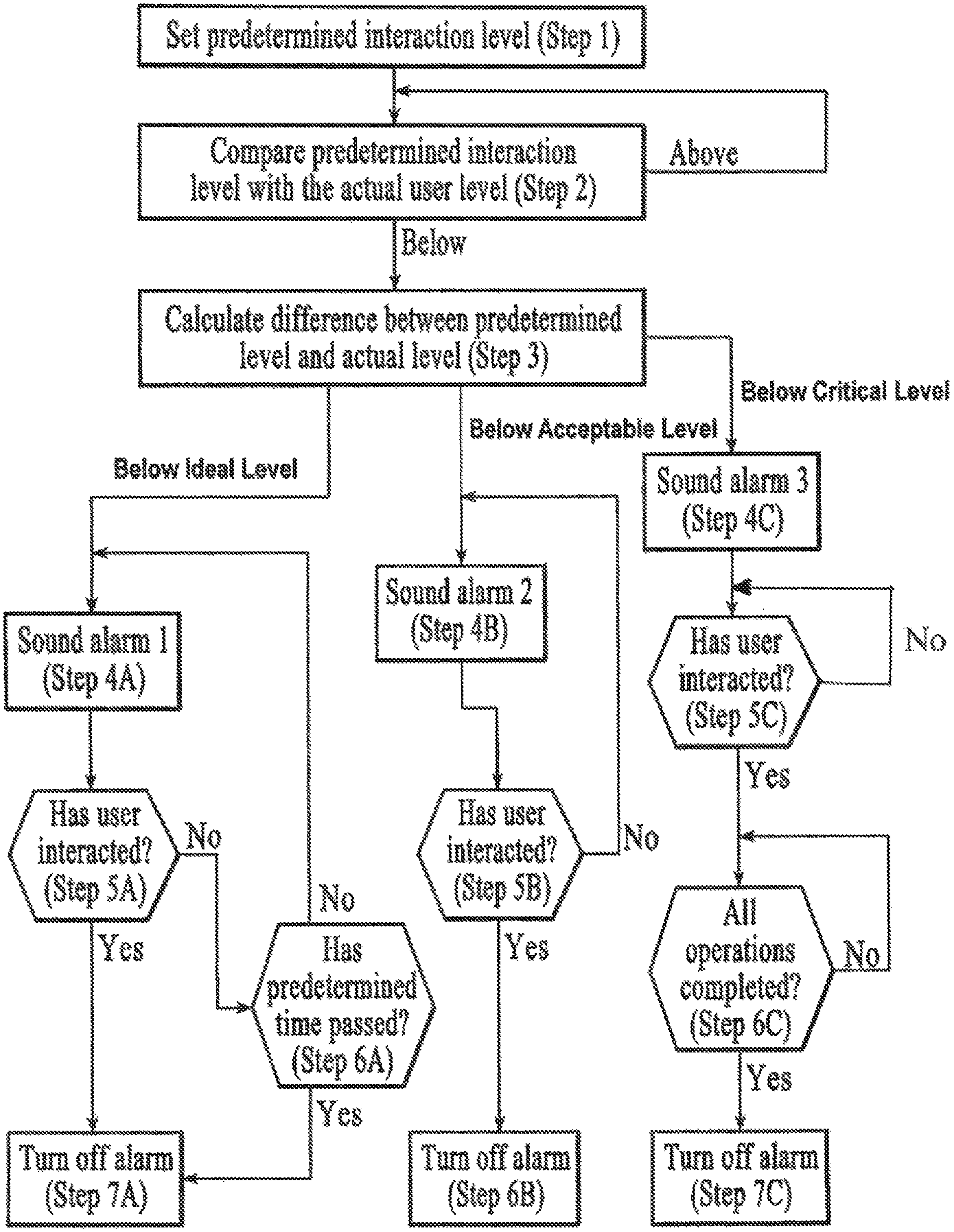
FIG. 6 is a chart of an analyte monitoring system according to an exemplary embodiment of the present disclosure.

FIG. 6 shows a chart according to an exemplary embodiment of the analyte monitoring system 100 of the present disclosure. As shown in Step 1 of FIG. 6, the predetermined target level of interaction is set. As discussed above, this level may be set by a user, an HCP, any other authorized person, or may automatically change depending on the factors discussed above. Next, in Step 2, the predetermined target level of user interaction is compared to the actual level of user interaction. If the user's actual level of interaction is above the predetermined target level, the system may simply wait. However, if the user's actual level of interaction falls below the target level, the system moves on to Step 3. In Step 3, the system calculates the difference between the actual level of user interaction and the predetermined target level.

In the exemplary embodiment shown in FIG. 6, there are three levels of user interaction, the "ideal," the "acceptable"

and the "critical" level of interaction. In this exemplary embodiment, if the user's actual level of interaction falls below the "ideal" target level of user interaction, the user may be prompted to interact with the device (Step 4A). In one exemplary embodiment, the device will sound a low volume alarm for a predetermined period of time. That is, in Step 5A, the device will determine if the user has interacted with the device, and if the user has interacted, the alarm is turned off (Step 7A). As described above, the user may interact with the device by pressing a button or the like. If the user has not interacted with the device, the device determines whether a predetermined period of time has passed (Step 6A), and if it has, turns off the alarm.

Similarly, if the user's actual level of interaction falls below the "acceptable" target level of interaction, the system will prompt the user to interact with the device, by sounding an alarm or the like (Step 4B). In this example, as shown in Steps 5B and 6B, the alarm will not be turned off until the user has acknowledged the alarm, by pressing a button or the like.

If the user's actual level of interaction falls below the "critical" target level of interaction, the system will set off a third alarm (Step 4C). Similar to the "acceptable" target level, the alarm will not be turned off until the user has acknowledged the alarm (Step 5C). Additionally, to silence an alarm corresponding to the "critical" target level of interaction, the user may be required to perform a series of operations (Step 6C). Once the user completes the series of operations, the alarm is turned off (Step 7C).

One of ordinary skill in the art will understand that the analyte monitoring system of FIG. 6 is simply one possible example of the system according to the present disclosure. Steps other than those described in FIG. 6 may be included in the analyte monitoring system, and similarly, the system does not have to include all of the steps shown in FIG. 6. As such, FIG. 6 should not limit the present disclosure in any way, and is simply provided as one example of an analyte monitoring system according to an embodiment of the present disclosure.

As shown in FIG. 2, the receiver unit (104 or 106) may also include a transmitter 30 which can be used to transmit a signal to activate an alarm system (not shown) on the data processing unit 102. In one exemplary embodiment, the data processing unit 102 may include a receiver for communicating with the receiver units 104 or 106. In another exemplary embodiment, the data processing unit 102 may include an alarm system (not shown) such as the one included with the receiver units 104 and 106, wherein the alarm of the data processing unit 102 may be activated by a receiver unit (104 or 106).

A receiver unit (104 or 106) may also include a number of optional items. One such item may be, for example, a data storage unit 28. The data storage unit 28 may be used to store the history of user interaction with the receiver unit, among other data. The data storage unit 28 may also be useful to store data that may be downloaded to another receiver unit, such as the primary receiver unit 104. Alternatively, the data may be downloaded to a computer or other data storage device in a user's home, at an HCP's office, etc., for evaluation of trends in analyte levels.

In one exemplary embodiment, the HCP may use the recorded history of interaction to modify the treatment of the user. The storage unit 28 may also store behavior variables, such as events, together with the data of the particular event. These behavior variables may be generated either automatically by the receiver unit or can, alternatively, be input by the user. In an exemplary embodiment, the user may also edit the event history. Examples of events may include things such as the user's activity level, state of health, medication (e.g., insulin) dosages, meals or any other event that may have an effect on the assessment of a treatment approach and recommendations for treatment modifications of the user.

As shown in FIG. 2, another optional component for the receiver unit is an input device 32, such as a keypad or keyboard. The input device 32 may allow numeric or alphanumeric input. The input device 32 may also include buttons, keys, or the like which initiate functions of, and/or provide input to, the analyte monitoring system 100. Such functions may include interacting with a receiver unit, manually changing the target level of user interaction with the receiver unit, changing the settings of the receiver unit or entering behavior variables to be used together with the history of user interaction with the receiver unit, but are not limited to the above.

Referring to FIG. 5, there is provided an exemplary embodiment of a receiver unit. In FIG. 5, the user may interact with the receiver unit using input options 32*a-d*. In one exemplary embodiment, input options 32*a* and 32*b* are used to select the options shown on the display 24, while input options 32*c* and 32*d* are used to move through lists to highlight options and change settings. In another exemplary embodiment, a user's interaction with the integrated test strip, used to, for example, manually check the blood analyte level of a user, can be included as part of the user's interaction with the device.

In one exemplary embodiment, the user will have to acknowledge the alarm or message displayed by the receiver unit (104 or 106). In this exemplary embodiment, a receiver unit (104 or 106) may have a button which is the default button for acknowledging an alarm or message. However, some alarms may require the user to interact with a button other than the default button. Further, in certain exemplary embodiments, some alarms may require the user to perform a series of operations, such as pressing a combination of buttons or the like, in order to silence the alarm.

Another exemplary embodiment of the input device 32 is a touch screen display. The touch screen display may be incorporated into the display 24 or may be a separate display. The touch screen display is activated when the user touches the screen at a position indicated by a "soft button" which corresponds to a desired function.

In addition, the analyte monitoring system 100 may include password protection to prevent the unauthorized transmission of data to a terminal or the unauthorized changing of settings for the system 100. A user may be prompted by the receiver unit to input a password using the input device 32 whenever a password-protected function is initiated.

Accordingly, a method in one aspect includes monitoring a user's actual frequency of interaction with the medical device, comparing the user's actual frequency of interaction with the medical device to at least one predetermined target level of interaction, and alerting the user when the user's actual frequency of interaction with the medical device is equal to or below the at least one predetermined target level of interaction.

In one aspect, alerting the user may indicate a difference between the actual frequency of interaction with the medical device and the predetermined target level of interaction.

The user may be alerted by an audible alarm, where the audible alarm may increase in loudness over time after being activated.

In another aspect, the user may be alerted by a vibrating alarm.

The method in a further embodiment may include a plurality of predetermined target levels of interaction, where alerting the user distinguishes between the plurality of target levels of interaction.

The user may be required to perform at least one step to turn off the alert, where the at least one step may be a decision related to the user's state of health.

The at least one predetermined target level of interaction may be adjusted by an authorized user.

In a further aspect, the method may include adjusting the at least one predetermined target level of interaction according to a time of day.

The method may also include adjusting the at least one predetermined target level of interaction according to a type of activity.

Also, the method may still include adjusting the at least one predetermined target level of interaction according to a future analyte level of the user, predicted using rate of change data.

Additionally, the method may include recording a history of the user's actual frequency of interaction with the medical device, where the method may also include adjusting the at least one predetermined target level of interaction according to the recorded history.

In still yet a further embodiment, the method may include organizing the history of the user's actual frequency of interaction with the medical device according to behavior variables inputted by the user.

Further, the method may include rewarding the user when the actual frequency of interaction stays above the at least one predetermined level of interaction for a predetermined time.

Additionally, the method may include adjusting the at least one predetermined target level of interaction according to a data received from a sensor located on the user.

An analyte monitoring system in accordance with another embodiment includes a user interactive analyte device to monitor at least one analyte of a user, and a processor unit coupled to the user interactive device to determine the frequency of user interaction with the analyte monitoring device.

The analyte may include glucose.

In still yet a further aspect, the user interactive device may include an in vivo analyte sensor, where the sensor may be configured to at least be partially positioned under a skin surface of a user.

An analyte monitoring system in accordance with still another embodiment may include a sensor to monitor an analyte level of the user, a transmitter to transmit information obtained by the sensor, and a receiver unit comprising a receiver to receive data from the sensor, and a display coupled to the receiver to display the received data to the user when the user interacts with the receiver unit, where the receiver unit monitors the user's actual frequency of interaction with the device, compares the user's actual frequency of interaction with the receiver unit to at least one predetermined target level of interaction, and alerts the user when the user's actual frequency of interaction with the receiver unit is equal to or below the at least one predetermined target level of interaction.

The system in one aspect may include a data storage unit for storing a history of the user's actual interaction with the receiver unit.

The receiver unit may be portable.

The receiver unit may include a user input unit for interacting with the display unit.

Further, the user input unit may be used to change settings of the receiver unit.

Although the exemplary embodiment of the present disclosure have been described, it will be understood by those skilled in the art that the present disclosure should not be limited to the described exemplary embodiments, but various changes and modifications can be made within the spirit and the scope of the present disclosure. Accordingly, the scope of the present disclosure is not limited to the described range of the following claims.

What is claimed is:

1. A method of glucose monitoring, comprising:

periodically receiving, via wireless communication and by a software on a remote receiving device, glucose level information from a data processing unit over a period of time, wherein the glucose level information is based on a signal generated by a glucose sensor having a distal portion configured to extend beneath a user's skin surface to be in contact with bodily fluid, the signal corresponding to a glucose concentration of the bodily fluid, and wherein the remote receiving device comprises a user interface comprising a touch-sensitive display;

determining, by the software on the remote receiving device, a frequency of user interaction with the remote receiving device over the time period based on user operation of the user interface;

displaying an output on the touch-sensitive display corresponding to the frequency of user interaction.

2. The method of claim 1, wherein the output includes average glucose views per day.

3. The method of claim 1, wherein the remote receiving device comprises at least one of a wristwatch, a portable computer, and a smartphone.

4. The method of claim 1, wherein the wireless communication comprises Bluetooth enabled communication.

5. The method of claim 1, wherein the user operation comprises an operation to obtain the glucose level using the touch-sensitive display.

6. The method of claim 1, wherein the software on the remote receiving device periodically receives glucose level information from the data processing unit after establishing a wireless communication channel between the software on the remote receiving device and software on the data processing unit by synchronizing the software on the remote receiving device with the software on the data processing unit to uniquely identify the data processing unit using an identification information of the data processing unit.

7. The system of claim 1, wherein the remote receiving device is configured to display a graph of glucose level information over the period of time on the touch-sensitive display.

8. The system of claim 1, wherein the user interface is configured to enable a user to choose a display mode using the touch-sensitive display.

9. The system of claim 8, wherein the user interface is configured to enable the user to choose a first display mode or a second display mode, the first display mode including blood glucose concentration and a second display mode including a graph of blood glucose concentration versus time.

10. The system of claim 1, wherein the user interface is configured to display an arrow showing a direction of a change in glucose level based on the signal over the period of time.

11. The system of claim 1, wherein the user interface is configured to display a color-coded indicator.

12. The system of claim 1, wherein the user interface is configured to display an indicator corresponding to the rate of change of the glucose level.

13. The system of claim 1, wherein the user interface is configured to display an indicator corresponding to acceleration in the rate of change of the glucose level.

14. A glucose monitoring system, comprising:

a glucose sensor having a distal portion configured to extend beneath a user's skin surface to be in contact with bodily fluid and to generate a signal corresponding to a glucose concentration of the bodily fluid;

a data processing unit operatively coupled to the glucose sensor and configured to receive the signal corresponding to the glucose concentration of the bodily fluid;

a remote receiving device, wherein the remote receiving device comprises a user interface comprising a touch-sensitive display and the is configured to:

periodically receive a glucose level information from the data processing unit over a period of time via wireless communication, wherein the glucose level information is based on the signal corresponding to the glucose concentration of the bodily fluid;

determine a frequency of user interaction with the remote receiving device over the time period based on user operation of the user interface; display an output on the touch-sensitive display corresponding to the frequency of user interaction.

* * * * *